United States Patent
Guo et al.

(10) Patent No.: US 12,054,467 B2
(45) Date of Patent: Aug. 6, 2024

(54) FLUIDIZED REACTION METHOD FOR SYNTHESIZING PROPYLENE OXIDE BY GAS PHASE EPOXIDATION OF PROPYLENE AND HYDROGEN PEROXIDE

(71) Applicants: DALIAN UNIVERSITY OF TECHNOLOGY, Liaoning (CN); DALIAN QIYUAN TECHNOLOGY CO., LTD., Liaoning (CN)

(72) Inventors: Hongchen Guo, Liaoning (CN); Quanren Zhu, Liaoning (CN); Cuilan Miao, Liaoning (CN)

(73) Assignees: DALIAN UNIVERSITY OF TECHNOLOGY, Liaoning (CN); DALIAN QIYUAN TECHNOLOGY CO., LTD., Liaoning (CN)

( * ) Notice: Subject to any disclaimer, the term of this patent is extended or adjusted under 35 U.S.C. 154(b) by 748 days.

(21) Appl. No.: 17/296,210

(22) PCT Filed: Apr. 14, 2020

(86) PCT No.: PCT/CN2020/084657
§ 371 (c)(1),
(2) Date: May 21, 2021

(87) PCT Pub. No.: WO2020/248696
PCT Pub. Date: Dec. 17, 2020

(65) Prior Publication Data
US 2022/0009897 A1    Jan. 13, 2022

(30) Foreign Application Priority Data
Jun. 14, 2019  (CN) .......................... 201910515976.5

(51) Int. Cl.
*C07D 301/12* (2006.01)
*B01J 8/18* (2006.01)
(Continued)

(52) U.S. Cl.
CPC .............. *C07D 301/12* (2013.01); *B01J 8/18* (2013.01); *B01J 29/89* (2013.01); *B01J 35/40* (2024.01);
(Continued)

(58) Field of Classification Search
CPC ........ C07D 301/12; C07D 303/04; B01J 8/18; B01J 29/89; B01J 35/40; B01J 37/0009;
(Continued)

(56) References Cited

FOREIGN PATENT DOCUMENTS

| CN | 1413768 A | 4/2003 |
| CN | 101850986 A | 10/2010 |

(Continued)

OTHER PUBLICATIONS

Charle B Khouw; "Catalytic Activity of Titanium Silicates Synthesized in the Presence of Alkali Metal and Alkaline Earth Ions;" Journal of Catalysis 12 31, 1995, pp. 77-86.

*Primary Examiner* — Taylor V Oh
(74) *Attorney, Agent, or Firm* — Muncy, Geissler, Olds & Lowe, P.C.

(57) ABSTRACT

A fluidized reaction method for synthesizing propylene oxide by gas phase epoxidation of propylene and hydrogen peroxide relates to a microspherical alkali metal ion modified titanium silicalite zeolite TS-1 catalyst applicable to the reaction method, and a preparation method thereof. A gas-solid phase fluidized epoxidation method refers to a gas phase epoxidation method in which the raw materials of propylene and hydrogen peroxide are directly mixed in the gas phase under normal pressure and temperature above 100° C. and the feed gas enables the titanium silicalite zeolite TS-1 catalyst to be fluidized in an epoxidation reactor. A catalyst applicable to the reaction method is a microspherical alkali metal ion modified titanium silicalite zeolite TS-1 catalyst which has the main characteristic that (Continued)

alkali metal cations are reserved on the titanium silicalite zeolite.

10 Claims, 5 Drawing Sheets

(51) Int. Cl.
  *B01J 29/89* (2006.01)
  *B01J 35/40* (2024.01)
  *B01J 37/00* (2006.01)
  *B01J 37/04* (2006.01)
  *B01J 37/06* (2006.01)
  *B01J 37/08* (2006.01)
  *B01J 37/10* (2006.01)

(52) U.S. Cl.
  CPC ......... *B01J 37/0009* (2013.01); *B01J 37/009* (2013.01); *B01J 37/04* (2013.01); *B01J 37/06* (2013.01); *B01J 37/082* (2013.01); *B01J 37/10* (2013.01); *B01J 2229/18* (2013.01)

(58) Field of Classification Search
  CPC . B01J 37/009; B01J 37/04; B01J 37/06; B01J 37/082; B01J 29/405; B01J 35/51; B01J 37/10; B01J 2229/18; B01J 2229/183; Y02P 20/52
  USPC .......................................................... 549/523
  See application file for complete search history.

(56) References Cited

FOREIGN PATENT DOCUMENTS

| | | |
|---|---|---|
| CN | 102320619 A | 1/2012 |
| CN | 102502688 A | 6/2012 |
| CN | 102502689 A | 6/2012 |
| CN | 103214001 A | 7/2013 |
| CN | 103347867 A | 10/2013 |
| CN | 105524018 A | 4/2016 |
| CN | 109251193 A | 1/2019 |
| CN | 110256376 A | 9/2019 |
| EP | 1085017 B1 | 5/2005 |
| WO | WO-2004029032 A1 | 4/2004 |
| WO | WO-2012048527 A1 | 4/2012 |
| WO | WO-2013063893 A1 | 5/2013 |

FLUIDIZED REACTION METHOD FOR SYNTHESIZING PROPYLENE OXIDE BY GAS PHASE EPOXIDATION OF PROPYLENE AND HYDROGEN PEROXIDE

TECHNICAL FIELD

The present invention belongs to the technical field of petrochemical industry, and relates to a fluidized reaction method for synthesizing propylene oxide by gas phase epoxidation of propylene and hydrogen peroxide, a microspherical alkali metal ion modified titanium silicalite zeolite TS-1 catalyst applicable to the reaction method, and a preparation method thereof.

BACKGROUND

Propylene oxide (PO) is one of the major derivatives of propylene. It is mainly used for producing polyether polyol and polyester polyol. The latters react with polyisocyanate to produce various polyurethane products (soft, semi-rigid and rigid). It is also used for producing propylene glycol and propylene glycol ether.

The traditional production technologies of propylene oxide include the chlorohydrin method and the co-oxidation methods. The main disadvantage of the chlorohydrin method is high pollution, while the main disadvantages of the co-oxidation methods (including the ethylbenzene co-oxidation method, the isobutane co-oxidation method and the cumene co-oxidation method) are large amount of co-products and complex technology.

A titanium silicalite zeolite is a silicate zeolite containing titanium heteroatoms in its crystal framework. TS-1 is a very important member of a titanium silicalite zeolite family It has excellent catalytic performance for the epoxidation of propylene and hydrogen peroxide.

MarcoTaramasso et al. first reported the synthesis method of TS-1 (GB2071071A, U.S. Pat. No. 4,410,501, 1983). TS-1 also has the same MFI topological structure and ten-membered ring cross-channel system as the well-known silica-alumina zeolite ZSM-5.

A large number of basic researches show that the titanium heteroatoms exist in the TS-1 framework in isolated tetra-coordinate form. The titanium heteroatoms generate characteristic absorption of electronic transition from oxygen ligand to titanium center atom near 210 nm in the UV-visible diffuse reflectance spectroscopy and generate characteristic resonance absorption near 1120 $cm^{-1}$ in the UV Raman spectroscopy. In addition, framework titanium species also generates characteristic absorption of Si—O—Ti asymmetric stretching vibration (or Si—O bond stretching vibration disturbed by framework titanium) at 960 $cm^{-1}$ in the intermediate infrared region of the infrared spectrum. The local environment of the framework titanium can be changed. According to the report of J. Catal., 1995, 151, 77-86, after sodium exchange is conducted on TS-1 with 1 M NaOH solution at 25° C., the infrared characteristic peak of the framework titanium of TS-1 zeolite near 960 $cm^{-1}$ disappears, and at the same time, new infrared characteristic absorption appears at 985 $cm^{-1}$. Some literature suggests that the sodium exchange that occurs in the strong alkaline solution is essentially the reaction of sodium hydroxide and the silicon hydroxyl near the framework titanium (NaOH+Si-OH→Si—O⁻ Na⁺+$H_2O$), which changes the local environment of the framework titanium, thereby influencing the infrared spectrum characteristics of the framework titanium.

A large number of application researches show that the TS-1 zeolite has wide applications. In short, TS-1 can catalyze the epoxidation reactions of low-concentration hydrogen peroxide and a series of olefins to form epoxides. In addition, TS-1 can also be used as a catalyst for hydroxylation of phenol, ammoxidation of cyclohexanone and oxidation of alcohols to produce aldehydes and ketones, and oxidation of alkane to produce alcohols and ketones. Neri et al. first reported a liquid phase epoxidation method of propylene by taking methanol as a solvent and 30 wt. % hydrogen peroxide as an oxidant (U.S. Pat. No. 4,833,260, 1989), and obtained the result that the hydrogen peroxide conversion rate and the propylene oxide (PO) selectivity are larger than 90%. Clerici et al. systematically studied the reactions of various lower olefins and hydrogen peroxides catalyzed by TS-1 (J Catal, 1993, 140(1): 71), and pointed out the order of the liquid phase epoxidation rate of olefins in various solvents is: methanol>ethanol>tert-butanol In 2008, the combination of the propylene liquid phase epoxidation (HPPO) technology based on TS-1 titanium silicalite zeolite and methanol solvent with the anthraquinone method for producing hydrogen peroxide was first commercialized by Degussa and Uhde, and BASF and Dow, respectively, to build a green factory for producing propylene oxide (Ind. Eng. Chem. Res. 2008, 47, 2086-2090).

Compared with the traditional production technologies of propylene oxide, the main advantage of the liquid phase epoxidation technology (HPPO) of propylene and hydrogen peroxide is that the reaction of propylene and hydrogen peroxide only produces propylene oxide and water. It does not have the problems of equipment corrosion, environmental pollution and co-products. However, the HPPO process must use a large amount of solvent to ensure that the propylene (oily) and hydrogen peroxide aqueous solution can become a stable homogeneous phase through liquid-liquid mixing, so that the epoxidation can be conducted safely. The methanol solvent is considered to be the most suitable solvent for the liquid phase epoxidation reaction of the propylene. In addition to wide sources, low price and common sense of solvent action, methanol is also considered to participate in the activation process of the hydrogen peroxide possibly by forming a so-called "five-membered ring" transition state with hydrogen peroxide molecules and framework titanium active sites. Therefore, compared with other solvents, methanol is considered to have an additional effect of promoting the activation of the hydrogen peroxide and the epoxidation. This is also the reason that current production devices of the HPPO technology use methanol as solvent. However, methanol solvent also brings big trouble to the practical application of the HPPO technology. Firstly, methanol easily causes solvolysis side reactions with the propylene oxide product, which results in high-boiling propylene glycol monomethyl ether and other by-products. These by-products not only remarkably reduce the selectivity of the propylene oxide, but also increase the difficulty of wastewater treatment. Secondly, the methanol solvent must be recycled and needs complex purifying treatment (including hydrogenation, rectification and resin adsorption) before recycled, this makes the HPPO technology complicated and investment and energy consumption increased. In addition, although the recycled methanol solvent will be treated by a complex purification process, more than ten or even 20 or 30 kinds of trace impurities (including fusel, aldehyde, ether, ester and acetals) are still difficult to be removed. These trace impurities will be recycled back to the reactor together with methanol solvent, consequently accelerate the deactivation of the epoxidation catalyst and greatly shortens the service cycle and life of the catalyst. There is no doubt that the problems caused by the use of the solvent have greatly weakened the competitive advantage of the HPPO technology.

We have been engaged in the exploratory research of the gas phase epoxidation of propylene and hydrogen peroxide since 2002. Said gas phase epoxidation is conducted under normal pressure and a temperature above 100° C. Under this condition, the reactants of propylene and hydrogen peroxide are directly mixed in the form of gas molecules, and the two reactants can penetrate through a TS-1 zeolite catalyst bed together to steadily conduct the epoxidation. Therefore, no solvent is required for mediation. The gas phase epoxidation technology of propylene and hydrogen peroxide does not use any solvent, and thus it can fundamentally overcome the problems of the current HPPO technology and is expected to become a new and more desired technology for the production of propylene oxide.

We have developed a dielectric barrier discharge plasma technology that can directly synthesize high-purity gaseous hydrogen peroxide from the mixture of hydrogen and oxygen, which has been documented in the following literature: Chem. Commun., 2005, 1631-1633; Modern Chemical Industry, Vol. 26 Supplement, 2006, P194-197; AIChE J, 53: 3204-3209, 2007; Advanced Technology of Electrical Engineering and Energy, Vol 28, 2009, No. 3, P73-76; Chin. J. Catal., 2010, 31: 1195-1199; CIESC Journal Vol 63, 2012, No. 11, P3513-3518; Journal of Catalysis 288 (2012) 1-7; Angew. Chem. Int. Ed. 2013, 52, 8446-8449; AIChE J, 64: 981-992, 2018; Chinese invention patents (application numbers) 200310105210.9, 200310105211.3 and 200310105212.8. In situ continuous synthesis of hydrogen peroxide gas was realized by using the plasma technology, and the first stage of research work related to the gas phase epoxidation of propylene was completed in 2007 (Zhou Juncheng. Direct synthesis of hydrogen peroxide by hydrogen and oxygen plasma method and its application in gas phase epoxidation of propylene [D]. Dalian: Dalian University of Technology, 2007). Specifically, a specially designed two-stage integrated reactor was used in the research work. The first stage reactor was a dielectric barrier discharge (DBD) plasma reactor for providing continuous and stable gaseous hydrogen peroxide feed for the epoxidation stage by using the mixture of hydrogen and oxygen as raw material (the concentration of the oxygen in the hydrogen is less than 6 v %). The second stage reactor was a gas phase epoxidation fixed bed reactor of propylene and gaseous hydrogen peroxide, it contained TS-1 zeolite particles. In the research, the results of the gas phase epoxidation obtained at 90° C. and 1 atm were: about 7% of propylene conversion rate, 93% of propylene oxide (PO) selectivity, and 0.24 kg PO kgPO kg TS-1$^{-1}$ h$^{-1}$ propylene oxide yield. Later, we carried out a more comprehensive research work by using the same epoxidation system and a micron-sized large-crystal TS-1 zeolite (unmodified) synthesized with a non-classical method (also known as the cheap method) as catalyst. The results published on Chin. J. Catal., 2010, 31: 1195-1199 indicate that at the reaction temperature of 110° C., the selectivity of the propylene oxide is increased to about 95%, and the yield of the propylene oxide is maintained to about 0.25 kg PO kg TS-1$^{-1}$ h$^{-1}$. The reaction activity of the catalyst is stable for at least 36 h in the gas phase epoxidation. However, the epoxidation selectivity, i.e., the utilization rate, of the hydrogen peroxide is only about 36%.

We have already noted that in addition to our preliminary work, Klemm et al. also reported the research work related to the gas phase epoxidation of propylene in 2008 [Ind. Eng. Chem. Res. 2008, 47, 2086-2090]. They provided gaseous hydrogen peroxide raw material for the gas phase epoxidation by using a special glass carburetor or a micro-channel falling-film evaporator and 50 wt % aqueous hydrogen peroxide solution. The gas phase epoxidation reactor was a micro-channel reactor with TS-1 zeolite coated inside. The reaction results obtained at 140° C. and 1 atm were: selectivity of propylene oxide was larger than 90%, and the yield of propylene oxide was larger than 1 kg PO kg$_{TS-1}$$^{-1}$. However, the utilization rate of the hydrogen peroxide was only about 25%.

The above preliminary research work about the gas phase epoxidation of propylene indicates that in the absence of the methanol solvent, the direct contact of propylene and hydrogen peroxide gas can effectively conduct the epoxidation over TS-1 zeolite, a considerable yield of the propylene oxide product can be obtained. Moreover, the selectivity of propylene oxide can be as high as about 90%, which is very close to the result of liquid phase epoxidation. This shows that the gas phase epoxidation technology of propylene and hydrogen peroxide has important development value.

However, when the gas phase epoxidation is conducted at high temperature (e.g., 110-140° C.), the self-decomposition side-reaction of $H_2O_2$ competes with the main epoxidation of hydrogen peroxide fiercely. The decomposition reaction of hydrogen peroxide (to produce water and oxygen) can occur on the material surface of the reactor or on the catalyst. The researches of Su Ji et al. (Journal of Catalysis 288 (2012) 1-7) and Ferrandez et al. [Ind. Eng. Chem. Res. 2013, 52, 10126-10132] indicate that the use of a TS-1 zeolite catalyst with low content of non-framework titanium and the use of relatively inert reactor material are beneficial to inhibit the self-decomposition of hydrogen peroxide. However, even if these measures are taken, in the previous researches, under the normal molar ratio of propylene and hydrogen peroxide, the epoxidation selectivity, that is, the utilization rate, of hydrogen peroxide can only be less than 40%. The utilization rate level of hydrogen peroxide is much lower than that of the liquid phase epoxidation (which is generally 85-95%). The serious problem of hydrogen peroxide decomposition at high temperature poses a major challenge for the development work of the gas phase epoxidation technology of propylene and hydrogen peroxide. This is because the rapid decomposition of hydrogen peroxide at high temperature not only reduces the utilization rate of hydrogen peroxide, wastes the raw material and increases the circulation of propylene, but also produces oxygen which easily makes the organic gas in the reaction system and the downstream separation system have an explosive composition and thus increases the risk of explosion accidents.

Thus, we have disclosed two TS-1 zeolite modification methods in the invention patents applied previously. The first method is to treat the TS-1 zeolite using the mixed solution of the tetrapropylammonium hydroxide (TPAOH) and inorganic salt (lithium, sodium, potassium and mixtures thereof) (Chinese invention patent (application number) 201110338224.x); and the second method is to treat the TS-1 zeolite using the mixed solution of tetrapropyl quaternary ammonium cation halide and inorganic base (alkali metal hydroxides of lithium, sodium and potassium) (Chinese invention patent (application number) 201110338451.2 and U.S. Pat. No. 9,486,790B2). The above two methods can obviously improve the catalytic performance of the gas phase epoxidation of the TS-1 zeolite, and the conversion rate of propylene can be increased to a maximum of 9%. However, the above two TS-1 zeolite modification methods cannot well solve the problem of high temperature decomposition of hydrogen peroxide in the gas phase epoxidation.

We recognize through subsequent research that a fixed bed reaction mode adopted in the previous work is an important factor leading to the low utilization rate of hydrogen peroxide. Moreover, the fixed bed reaction mode is not conducive to industrial application. Specifically, for the gas phase epoxidation of propylene and hydrogen peroxide, the fixed bed reaction mode has the following problems: (1) due to the high reaction temperature, propylene gas and gaseous hydrogen peroxide always conduct the gas phase epoxidation in the top thin layer of catalyst of a fixed bed reactor in the entire reaction cycle; and most catalysts beyond the thin layer have no chance to participate in the reaction, and the utilization rate of the catalyst is low. (2) Because the epoxidation of propylene and hydrogen peroxide is strongly exothermic, when the gas phase epoxidation is mainly conducted in the top thin layer of catalyst of the fixed bed reactor, the heat released by the epoxidation is concentrated in the small region, which is easy to form a temperature "hot spot". (3) The efficiency of removing the reaction heat from the fixed bed reactor is low; and thus the high temperature of the "hot spot" inevitably intensifies the side-reaction of the thermal decomposition of hydrogen peroxide. Due to the existence of the above problems, the fixed bed reactor has the problem of low utilization rate of hydrogen peroxide, and more importantly, the security risk of the fixed bed reactor will be increased dramatically when it is scaled up (the risk of forming the explosive gas mixture will be increased by organic compounds and molecular oxygen from the decomposition of hydrogen peroxide). Therefore, the technology of gas phase epoxidation based on fixed bed reactor is difficult to be industrialized.

So far, there are few public and patent reports on the gas phase epoxidation of propylene and hydrogen peroxide in China and abroad. We have noted that the epoxidation reactor adopted by Ferrandez et al. in the research work on the gas phase epoxidation of propylene reported in 2013 [Ind. Eng. Chem. Res. 2013, 52, 10126-10132] belongs to the fixed bed. The gas phase epoxidation of propylene research work reported by Klemm et al. in 2008 [Ind. Eng. Chem. Res. 2008, 47, 2086-2090] involves a microchannel reactor which is coated with TS-1 catalyst. The microchannel reactor can avoid the temperature "hot spot", but it is very expensive, difficult to scale up, and therefore not suitable for the production of bulk chemicals such as propylene oxide.

In addition, in the follow-up research, we realized that the two disclosed TS-1 zeolite modification methods in the inventions applied previously by us (Chinese invention patent (application number) 201110338224.x, Chinese invention patent (application number) 201110338451.2 and US Patent U.S. Pat. No. 9,486,790B2) also have limitations in improving the gas phase epoxidation performance of propylene and hydrogen peroxide (the highest conversion rate of propylene for the modified TS-1 zeolite in the gas phase epoxidation reaction is ≤9%). This is because that, in these inventions we pursue for the dual applicability of the catalyst in both the liquid phase and gas phase epoxidations of propylene and hydrogen peroxide. Therefore, the two disclosed modification methods cannot lead to the TS-1 zeolite catalyst that is especially suitable for the gas phase epoxidation of propylene and hydrogen peroxide. The above invention patents have a common feature which underlines that the residual alkali metal ions in the modified TS-1 zeolite are not conducive to achieving the modification effect. Therefore, the patents clearly state in the technical solutions that, during the post-treatments, the TS-1 zeolite hydrothermally treated with a mixed solution containing the alkali metal ions must be fully washed with deionized water and the pH value of the filtrate should be less than 9 (the embodiment points out the pH is preferably 7).

It should be recognized that in our previous inventions the very strict restrictive requirements for the content of the alkali metal ions were put forward under the influence of the existing knowledge.

For example, J. Catal., 1995, 151, 77-86 has systematically shown the influence of sodium ion content on the TS-1 zeolite by adding sodium salt to the synthetic gel of TS-1. The data provided by the literature show that when the sodium ion content in the gel is too high (Na/Si molar ratio≥0.05), the synthesized TS-1 zeolite has no catalytic activity for n-octane oxidation; and only when the sodium ion content in the gel is very low (Na/Si molar ratio≤0.01), the catalytic activity of the synthesized TS-1 zeolite can close to a normal level. The data provided by the literature also show that although high sodium content can obviously reduce or even completely deactivate the epoxidation catalytic activity of the TS-1 zeolite, it can significantly promote the decomposition of hydrogen peroxide. Based on the results of the liquid phase oxidation reactions, the empirical value with the maximum allowable value of the alkali metal ions of 0.01 in the gel during the hydrothermal synthesis of the TS-1 zeolite is suggested (indicated by the molar ratio of the alkali metal ions to Si atoms, see J. Catal., 1995, 151, 77-86; Stud. Surf. Sci. Catal., 1991, 69, 79-92; Stud. Surf. Sci. Catal., 1991, 60, 343-352; Appl. Catal. A-gen., 2000, 200, 125-134; Front. Chem. Sci. Eng., 2014, 8, 149-155.).

In addition, Applied Catalysis A: General 200 (2000) 125-134 reports the practice of performing alkali metal ion exchange treatment on the TS-1 zeolite by using the potassium carbonate solution at room temperature. As the sodium exchange effect on TS-1 zeolite with 1 M NaOH solution reported by J. Catal., 1995, 151, 77-86, the potassium ion in the strong alkaline potassium carbonate solution can also conduct similar ion exchange reaction with the silicon hydroxyl near the framework titanium, which replaces the hydrogen ion on the silicon hydroxyl, thereby changing the local environment of the framework titanium and influencing the infrared spectrum characteristics of the framework titanium. However, from the provided results of the liquid phase oxidation reaction of hexane and 2-hexene, the alkali metal ion exchange treatment at room temperature reduces the catalytic activity of treated TS-1 zeolite.

Namely, people have known in the TS-1 zeolite synthesis research that the presence of the alkali metal ions in the hydrothermal synthesis system is unfavorable for the introduction of titanium into the framework of TS-1, and people have also discovered through ion exchange research that the introduction of the alkali metal ions into the TS-1 zeolite in the post-synthesis process is also unfavorable to the liquid phase oxidation reaction based on hydrogen peroxide oxidant.

It should be indicated that TS-1 zeolite framework often contains very low content of trivalent metal ion impurities (such as $Al^{3+}$ and $Fe^{3+}$) which may produce bridging hydroxyl groups with strong proton acidity. The very small amount of strong acid sites will cause acid-catalyzed side-reactions in the liquid phase oxidation reactions catalyzed by the TS-1 zeolite, thereby reducing the selectivity of the reaction. Therefore, Catal. Lett., 8, 237 (1991) and Stud. Surf. Sci. Catal., 84, 1853 (1994) have reported that the introduction of a very low content of alkali metal ions into such TS-1 zeolite can effectively prevent the acid sites from destroying the catalyst selectivity. However, in this case, the role of the very small content of alkali metal ions in TS-1 zeolite is counter cation which neutralizes the zeolitic acid sites, instead of modifying the framework titanium active site. For the liquid phase oxidation reaction, if the alkali metal ions introduced into the TS-1 zeolite exceed the amount required to neutralize the acid sites, then side effects such as reduction of catalyst activity would be caused.

In addition, those who skilled in the art know that, various low-temperature selective oxidation reactions catalyzed by the titanium silicalite zeolite use aqueous hydrogen peroxide solution as oxidant. The commercial hydrogen peroxide solution often contains 200-300 ppm acid stabilizer (50 wt. % $H_2O_2$ has a pH value of about 1-2). The acid stabilizer enters the titanium silicalite zeolite catalytic reaction system together with hydrogen peroxide, which will acidify the reaction medium (in the propylene epoxidation reaction medium, the pH value of the hydrogen peroxide-methanol feed (3 mol$H_2O_2$/L) is about 3.0), and will also reduce the reaction selectivity. In addition, when hydrogen peroxide molecules are activated on the titanium active site of the titanium silicalite zeolite through a "five-membered ring" manner, a transient peroxy proton (Ti($\Theta^2$)—O—$O^-$ $H^+$) with strong acidity is produced. In order to neutralize these acidic substances and proven their negative influence on the selectivity of the propylene epoxidation, many patents adopt the strategy of adding alkaline substances to the reaction medium. For example, the alkaline additives mentioned in the Chinese invention patent (application number) 201410512811.x are ammonia, amine, quaternary ammonium base and $M^1(OH)_n$. $M^1$ is alkali metal or alkaline earth metal. The additives mentioned in Chinese invention patent (application number) 00124315.2 are alkali metal hydroxide, alkali metal carbonate and bicarbonate, alkali metal carboxylate and ammonia. Chinese invention patent (application number) 03823414.9 claims the introduction into the reaction medium of less than 100 wppm alkali metal and alkaline earth metal, or alkali and alkali cation with a pKB value of less than 4.5, or the combination of alkali and alkali cation, wherein wppm is based on the total weight of hydrogen peroxide in the reaction mixture. Chinese invention patent (application number) 201180067043.6 claims that the addition of 110-190 micromoles potassium cations and phosphorus with at least one hydroxy acid anion into the reaction medium. The micromoles level loading of additive is based on 1 mole of hydrogen peroxide in the feed. Therefore, the existing literature tells us that the way to deal with the extrinsic acidity of the catalyst is to add alkaline substances to the reaction medium or mixture, including alkali metal hydroxides or weak acid salts that can release hydroxide ion via hydrolysis. The loadings of the alkaline substances are generally determined based on the amount of hydrogen peroxide in the feed. According to the information disclosed in the Chinese invention patent (application number) 201480052389.2, at least most of the alkaline substances added to the reaction medium can flow out of the reactor outlet along with the reaction products. Obviously, the above practice that adds a small amount of alkaline substances to the reaction medium, including the addition of alkali metal ions or hydroxides thereof to neutralize the acidity of the reaction medium and the transient peroxy protons produced by the activation of hydrogen peroxide by TS-1, are all not a practice of modifying the framework titanium active site. Applied Catalysis A: General 218 (2001) 31-38 pointed out that, in a batchwise propylene liquid phase epoxidation test, the attempt of introducing a small amount of sodium carbonate into the reactant, in order to increase the pH value of the reaction liquid, and consequently to further inhibit the side-reaction between the epoxidation product and the solvent, so as to enhance the selectivity of propylene oxide, can easily cause the deactivation of the catalyst due to the accumulation of sodium carbonate on the catalyst. The results in Table 5 in the literature show that if the loading of $Na_2O$ on TS-1 reaches 1.36 wt. % (approximately equivalent to Na/Si=0.027) by sodium carbonate impregnation, the catalyst activity (hydrogen peroxide conversion rate) may be reduced by nearly a half.

Of course, we have already known that Chinese invention patent (application number) 200910131992.0 discloses a method for hydrothermal modification of TS-1 using an aqueous solution of a mixture of organic base and inorganic base. The inorganic base involves ammonium hydroxide, sodium hydroxide, potassium hydroxide and barium hydroxide; and the organic base involves urea, quaternary ammonium base, fatty amine and alcohol amine compounds. Embodiments 2, 3, 4, 7, 8 and 11 of the patent respectively relate to the use of sodium hydroxide and ethylenediamine, potassium hydroxide and TPAOH, the potassium hydroxide and triethanolamine, sodium hydroxide and n-butylamine, the potassium hydroxide and TPAOH, and a base combination of the sodium hydroxide and TPAOH. In the above embodiments, the temperatures of hydrothermal modification are respectively 180° C., 150° C., 180° C., 120° C., 90° C. and 180° C. The invention uses the reaction of phenol hydroxylation to diphenol (liquid phase) and the reaction of cyclohexanone ammonia oxidation (liquid phase) to demonstrate the comprehensive improvement of activity, selectivity and activity stability of the modified zeolite. However, it is worth noting that the invention uses Fourier Transform Infrared Spectroscopy (FT-IR) to confirm that the modified TS-1 zeolites, including the modifications involved by the inorganic bases, show the same infrared absorption band of framework titanium at 960 cm$^{-1}$ as the unmodified matrix. Therefore, the patent uses the ratio of the absorption band intensity at 960 cm$^{-1}$ ($I_{960}$) to the absorption band intensity at 550 cm$^{-1}$ ($I_{550}$) to characterize the influence of mixed base modification on the relative content of the framework titanium. Chinese invention patent (application number) 200910131993.5 discloses a method for hydrothermal modification of the TS-1 zeolite using a pore-forming-agent containing aqueous solution of inorganic base and/or organic base. The inorganic base involves ammonium hydroxide, sodium hydroxide, potassium hydroxide and barium hydroxide. Embodiments 2 and 3 respectively relate to a sodium hydroxide modification solution containing starch and a potassium hydroxide modification solution containing polypropylene. Similar to Chinese invention patent (application number) 200910131992.0, the invention also uses the reaction of phenol hydroxylation to diphenol (liquid phase) and the reaction of cyclohexanone ammonia oxidation (liquid phase) to demonstrate the comprehensive improvement of activity, selectivity and activity stability of the modified zeolite. Moreover, the invention also uses Fourier Transform Infrared Spectroscopy (FT-IR) to confirm that the modified TS-1 zeolites, including the modifications involved by inorganic base, show the same infrared absorption band of the framework titanium at 960 cm$^{-1}$ as the matrix. Therefore, the patent also uses the ratio of absorption band intensity at 960 cm$^{-1}$ ($I_{960}$) to the absorption band intensity at 550 cm$^{-1}$ ($I_{550}$) to characterize the influence of base modification on the relative content of the framework titanium. The above inventions do not mention whether the modified TS-1 zeolite contains the alkali metal ions. The purpose of the invention is actually to improve the microporous diffusivity of the TS-1 zeolite through hydrothermal modification. However, the characterization results of Fourier Transform Infrared Spectroscopy (FT-IR) provided by the inventions show that, the modified TS-1 zeolites, including the modifications involved by the inorganic base, show the infrared absorption band of the framework titanium at 960 cm$^{-1}$, which is an important feature. It indicates that the use of the modification method provided by the above inventions, the alkali metal ions do not affect the asymmetric stretching vibration of the Si—O—Ti bond (or called the Si—O bond stretching vibration disturbed by the framework titanium). In other words, the alkali metal ions do not affect and change the local environment of the framework titanium The most reasonable explanation of this phenomenon is that most of the alkali metal ions that may contain in the modified TS-1 zeolite have been eliminated by the above-mentioned inventions via the generally adopted post-treatment steps, such as washing.

In addition, we also note that the following invention patents relate to alkaline solution treatment. However, the so-called alkaline solution treatment is not the modification for the framework titanium active site.

For example, the TS-1 moulding method disclosed in the Chinese invention patent (application number) 201010511572.8 relates to an alkaline solution treatment step, and the catalyst prepared by the patented method is used for propylene liquid phase epoxidation to produce propylene oxide. However, the patent has the following features. Firstly, a hollow TS-1 zelite ("hollow" means TS-1 has been subjected to a secondary hydrothermal modification. The method of the secondary hydrothermal modification can be seen in Chinese invention CN1132699C with application number 99126289.1) is moulded by using a silica sol as binder, said silica sol containing a kind of silane which has at least two hydrolysable groups, to obtain a molded body. Then, the molded body is subjected to heat treatment by the alkaline solution involving the sodium hydroxide, the potassium hydroxide, the tetramethylammonium hydroxide and tetraethylammonium hydroxide, and is dried and calcined to obtain the TS-1 catalyst which has enough anti-crushing strength and extra-high zeolite content. The temperature range of heat treatment is 60-120° C.; the concentration of the used alkaline solution is within the range of 0.1-10 mol %; and the ratio of the alkaline solution to the molded body is (0.5–5)/1. It can be clarified that the alkaline solution heat treatment involved in the invention is not used to modify the molded body, but is used to promote the hydrolysis reaction of silane and/or siloxane in the binder, so that the molded body obtains enough anti-crushing strength. This can be confirmed by the proposal in paragraph [0034] of the patent text ("the use amount of the alkali can be selected according to the amount of silane and/or siloxane with at least two hydrolyzable groups."). In addition, based on the comparative analysis of the heat treatment temperature, time and index data (particle strength, hydrogen peroxide conversion rate and propylene oxide selectivity) in embodiments 1-7, the upper limit of the heat treatment temperature of 120° C. in the patent corresponds to the lower limit of the treatment time of 2 hours. Namely, in order to achieve a good molding effect, the temperature of the alkaline solution heat treatment should not be high and the time should not be long; otherwise, the reaction activity and selectivity of propylene liquid phase epoxidation may be reduced Alkaline solution heat treatment conditions of 90° C. and 6 hours adopted in embodiment 4 are optimal values.

For another example, a preparation method of a high-performance titanium silicalite zeolite catalyst disclosed in the Chinese invention patent (application number) 201310146822.6 also relates to the step of modifying the micron-sized titanium silicalite zeolite with the alkaline solution. The main feature of the preparation method is that the micron-sized titanium silicalite zeolite is first treated with the alkaline solution for the purpose of manufacturing a large number of mesopores and macropores on the micron-sized titanium silicalite zeolite to improve the accessibility of the titanium active site inside the large-crystal titanium silicalite zeolite and facilitate the diffusion of product molecules from the interior of large crystals to the outside. Then, the titanium-containing modified solution is used to treat the titanium silicalite zeolite containing mesopores and macropores again, for the purpose of introducing more active sites to the surface of the zeolite through the crystallization process. It can be clarified that although alkali metal hydroxide is mentioned in the alkaline solution treatment step of the invention, the patent requires that the zeolite treated in the step needs to be washed to meet the requirement of neutral pH. This means that washing in the step must be very adequate. In this way, even if the alkali metal hydroxide is used to complete the modification treatment of the alkaline solution, the alkali metal ions may not be left on the catalyst. This is because hydroxyl anions may be left if the alkali metal ions are left, so that the harsh requirement of neutral pH cannot be met. The reason that the invention proposes such a high requirement for the step of washing is that the subsequent modification step is to introduce the framework titanium active site on the surface of the zeolite. Based on the above background introduction, it is not difficult to understand that if the zeolite is allowed to contain a large amount of alkali metal ions in the first step of alkaline solution treatment of the invention, it will inevitably prevent titanium from effectively entering the framework and becoming the active site in the second step of modification.

SUMMARY

In order to further improve the technical level of the gas phase epoxidation of propylene and hydrogen peroxide, the present invention provides a gas-solid phase fluidized reaction method, a microspherical alkali metal ion modified titanium silicalite zeolite TS-1 catalyst applicable to the reaction method, and a preparation method thereof.

The gas-solid phase fluidized reaction method of gas phase epoxidation of propylene and hydrogen peroxide in the present invention specifically refers to a gas phase epoxidation method in which the raw materials of propylene and hydrogen peroxide are directly mixed in the gas phase under normal pressure and temperature above 100° C. and the feed gas enables the titanium silicalite zeolite TS-1 catalyst to be fluidized in the epoxidation reactor. Based on research, we have found that the gas phase epoxidation of propylene and hydrogen peroxide is very rapid at a reaction temperature above 100° C., and it is sufficient for the reactants to complete the epoxidation if the contact time of within 60 milliseconds is allowed for the reactants to contact with the catalyst. Therefore, a bubbling bed, a turbulent bed, a fast bed or a transportation bed can be used for the gas-solid phase fluidized reaction. The gas-solid phase fluidized reaction mode has the following advantages: (1) the epoxidation catalysts suspended in the mixed feed gas of propylene and hydrogen peroxide are fluidized; the feed gas can be fully mixed and contacted with the catalysts; and all the catalysts can participate in the epoxidation. In this case, gaseous hydrogen peroxide molecules can contact with the active site of the epoxidation to the maximum extent in the first time, thereby obviously promoting the gas phase epoxidation between hydrogen peroxide and propylene and obviously suppressing the self-decomposition side reaction of hydrogen peroxide, so that the utilization rate of hydrogen peroxide in the gas phase epoxidation is obviously increased. (2) The epoxidation of propylene and hydrogen peroxide can occur homogeneously on all the catalysts; the reaction heat is dispersed; and no temperature "hot spot" is formed. (3) The fluidized reaction has a large heat transfer coefficient and is easy to remove heat and beneficial to control the reactor temperature in an optimal state. This advantage is beneficial for not only the reduction of the self-decomposition of hydrogen peroxide, but also the safety of industrial reactors, and is of great significance to industrialized application.

The key to the gas-solid phase fluidized reaction method is the use of a proper microspherical catalyst. The microspherical catalyst, which is applicable to the gas phase epoxidation fluidized reaction mode of propylene and hydrogen peroxide in the present invention, is a microspherical alkali metal ion modified titanium silicalite zeolite TS-1 catalyst. The preparation method of said microspherical catalyst has the following technical features: (1) the titanium silicalite zeolite TS-1 is subjected to a degree controlled hydrothermal treatment by using the alkali metal hydroxide solution. After the hydrothermal treatment, alkali metal cations must remain on the titanium silicalite zeolite, and at least part of the alkali metal cations are on the silicon hydroxyl near the framework titanium in the form of counter cations to modify the local environment of the framework titanium. Such a modification step is used to produce the framework titanium active sites that are more effective for the gas phase epoxidation. (2) The titanium silicalite zeolite TS-1 modified by alkali metal ions is mixed with a binder and is prepared as a slurry. The slurry is then used for spray shaping. The processing step is used to prepare a microspherical epoxidation catalyst which can meet the requirements of the gas-solid phase fluidized reaction.

In the technical solutions and the specific embodiments of the present invention, the preparation of the titanium silicalite zeolite catalyst is illustrated with TS-1 titanium silicalite zeolite. This is mainly because TS-1 is a very important member of a titanium silicalite zeolite family, and is the best representative. TS-1 is relatively easier to synthesize, it is widely reported in the literature, and used widely in industry. At present, it is the TS-1 zeolite which is commercially used in the HPPO technology of the liquid phase epoxidation of propylene and hydrogen peroxide.

The hydrothermal modification of the alkali metal hydroxide solution in the present invention preferably uses sodium hydroxide and potassium hydroxide solutions, and less preferably lithium hydroxide solution. Other alkali metal hydroxides (such as cesium hydroxide) also have similar modification effects, but are not recommended due to price and resource problems. After repeated researches, we are surprised to find that, after the titanium silicalite zeolite TS-1 being modified by the method of the present invention, the framework titanium modified by the alkali metal cations on the nearby silicon hydroxyl has almost no catalytic activity for the liquid phase epoxidation of propylene at low temperature with methanol as a solvent, but is a more efficient catalytic active site for the gas phase epoxidation of propylene and hydrogen peroxide in the absence of the solvent and at high temperature (which is generally higher than 100° C. under normal pressure). The alkali metal ion modified framework titanium active site can obviously inhibit the self-decomposition side-reaction of hydrogen peroxide at a normal propylene/hydrogen peroxide feed ratio and increase the conversion rate of propylene, so as to increase the utilization rate of hydrogen peroxide and reduce the generation of oxygen, thereby greatly improving the economy and the safety of the gas phase epoxidation.

In the present invention, the framework titanium active site of the titanium silicalite zeolite TS-1 modified by the degree controlled hydrothermal treatment of the alkali metal hydroxide solution can be properly modified by alkali metal ions and consequently has unique infrared spectrum characteristics. Specifically, in the infrared vibrational spectrum, the characteristic absorption peak of the framework titanium active site appropriately modified by the alkali metal ions appears in a range above 960 $cm^{-1}$ and below 980 $cm^{-1}$, it is a novel framework titanium active site that is different from the known tetra-coordinate framework titanium active site (infrared absorption is at 960 $cm^{-1}$) and the hexa-coordinate framework-like titanium active site $(Ti(OSi)_2(OH)_2(H_2O)_2)$ (UV Raman absorption peak is at 695 $cm^{-1}$). Although the literature (J. Catal., 1995, 151, 77-86) has reported that the sodium exchange of TS-1 with 1 M NaOH solution at 25° C. also changes the infrared spectral characteristics of TS-1 zeolite framework titanium (the absorption peak at 960 $cm^{-1}$ is shifted to a shoulder peak at 985 $cm^{-1}$), and that the sodium exchange conducted in the strong alkaline solution is also the exchange reaction between the sodium ion in the sodium hydroxide and the hydrogen proton on the silicon hydroxyl near the framework titanium $(NaOH+Si-OH \rightarrow Si-O^-+H_2O)$, and that the consequence of the exchange reaction is to make the sodium ion to exist on the silicon hydroxyl near the framework titanium in the form of counter cation, which would naturally change the local environment of the framework titanium. However, in the present invention, the infrared characteristic absorption of the framework titanium active site modified by the alkali metal ion appears in the range above 960 $cm^{-1}$ and below 980 $cm^{-1}$, which is different from the value (985 $cm^{-1}$) reported in the literature by at least 5 wave numbers ($cm^{-1}$). It is not difficult for people familiar with infrared spectroscopy to understand that two infrared absorptions with such a large difference in the wave numbers should belong to the vibration of different framework titanium sites. In addition, it will be seen from the reference embodiment provided by the present invention that the sodium exchange TS-1 zeolite prepared according to the method reported in J. Catal., 1995, 151, 77-86 (the framework titanium infrared characteristic absorption appears near 985 cm', which is consistent with the literature report) is basically inactive for the gas phase epoxidation of propylene and hydrogen peroxide. In sharp contrast to this, the sodium ion modified TS-1 zeolite obtained according to the present invention (the infrared characteristic absorption of the framework titanium appears in the range above 960 $cm^{-1}$ and below 980 $cm^{-1}$) has high activity and high selectivity for the gas phase epoxidation. People familiar with the titanium silicalite zeolite know that four framework silicons are first adjacent to the framework titanium. The four framework silicons are not equivalent in space. The four framework silicons have 16 possible hydroxyl positions. The relative positions of these silicon hydroxyls are quite different relative to the framework titanium site. We conclude from the study of quantum chemistry calculation that the difference of infrared spectral characteristics of the framework titanium of the alkali metal ion modified TS-1 provided by the present invention from the room temperature sodium exchange TS-1 reported in the literature, should be caused by the different silicon hydroxyl positions occupied by the alkali metal countercations.

The present invention discloses a method which tells how to use the alkali metal hydroxide solution to hydrothermally treat a zeolite of titanium silicalite with controlled degree. The phrase "controlled degree" is mainly used to explain that the hydrothermal treatment method provided by the present invention can ensure that the alkali metal ion is always located in the most favorable silicon hydroxyl position, so as to most favorably modify the local environment of the framework titanium site of the modified TS-1 zeolite, thereby more effectively promote the gas phase epoxidation of propylene and hydrogen peroxide.

Therefore, in general, the basic features of the gas phase epoxidation catalyst applicable to the fluidized reaction mode in the present invention are: (1) the titanium silicalite zeolite TS-1 is hydrothermally modified by the alkali metal hydroxide and contains a large amount of alkali metal ions; the typical ratio of the content of the alkali metal ions to the titanium content is not less than 0.1 (molar ratio); (2) at least a part of the alkali metal cations are located on the silicon hydroxyl near the TS-1 zeolite framework titanium in the form of counter cations which generate the most favorable modification upon the local environment of the framework titanium; and the modified framework titanium active site produces infrared characteristic absorption above 960 $cm^{-1}$ and below 980 $cm^{-1}$; (3) the final catalyst is a microspherical catalyst formed by spraying the above modified titanium silicalite zeolite TS-1 with binder. The average size of the catalyst microspheres is 60-80 microns; and the specific microsphere size distribution meets the requirements of the gas-solid phase fluidized reaction.

To realize the degree controlled hydrothermal treatment for the TS-1 zeolite in the present invention, firstly, a low-concentration alkali metal hydroxide solution is selected for hydrothermal treatment. Secondly, when the TS-1 zeolite is subjected to the hydrothermal treatment with the low-concentration alkali metal hydroxide solution, proper hydrothermal treatment temperature, time and liquid-solid ratio must also be adopted. In other words, the concentration of the alkali metal hydroxide solution, the temperature and time of the hydrothermal treatment, and the liquid-solid ratio are the basic parameters that control the degree of the hydrothermal treatment for the TS-1 zeolite.

In the present invention, the spray forming of the modified titanium silicalite zeolite can be conducted by the conventional methods. However, based on research, we have found that, in order to make the microspherical catalyst have good sphericity, crystal size distribution, abrasion resistance, epoxidation activity and selectivity, the slurry used for spray drying should preferably be prepared with the hydrolysate of tetraethyl orthosilicate; and the hydrolysis of the tetraethyl orthosilicate is preferably conducted under acidic conditions; and the hydrolysate is preferably dealcoholized before use.

The inventiveness of the present invention is mainly reflected in two aspects. In the first aspect, the present invention uses the gas-solid phase fluidized bed reaction mode for the epoxidation of propylene and hydrogen peroxide to synthesize propylene oxide for the first time. As described above, the gas-solid phase fluidized bed reaction mode has obvious superiorities over the fixed bed reaction mode reported in the previous literature. The superiorities at least include: the gas-solid phase fluidized bed reaction mode is beneficial to inhibit the self-decomposition side-reaction of hydrogen peroxide, beneficial to disperse the reaction heat and rapidly take away the heat, beneficial to improve the utilization rate of the catalyst and the production capacity of the unit catalyst, and beneficial to industrial application and industrial production safety. We have noted that the liquid-solid phase fluidized reaction modes such as a slurried bed (a slurry bed) are mentioned in the patent literature involving the liquid phase epoxidation of propylene; and the liquid-solid phase fluidized reaction modes such as the slurried bed (the slurry bed) appear in, for example, Chinese invention patents (application numbers) 200710099853.5, 201010511512.6, 201010511515.x and 201010511561.x. However, the liquid-solid phase fluidized reaction modes need to use the solvent. For the epoxidation of propylene and hydrogen peroxide, both the liquid-solid phase fluidized reaction mode and the liquid (solid) phase fixed bed reaction mode (that is, the reaction mode of the HPPO technology) use methanol as the solvent, and the methanol solvent also participates in hydrogen peroxide activation process in addition to act as the solvent of general sense. This is different from the solvent-free gas-solid phase fluidized propylene epoxidation of the present invention at least in the aspect of reaction mechanism. Besides, those skilled in the art know that there are other essential differences between the gas-solid phase fluidized reaction of the present invention and the liquid-solid phase fluidized reaction in the literature, including at least mass transfer resistance, reaction kinetics, operation mode, and requirements for the crystal size of the catalyst and mechanical strength. Therefore, the gas-solid phase fluidized reaction of the present invention and the liquid-solid phase fluidized reaction in the literature are two different types of technologies. In the other hand, the inventiveness of the present invention also lies in the use of the alkali metal hydroxide solution to conduct degree controlled hydrothermal treatment on the TS-1 zeolite for the first time. The modified TS-1 zeolite contains a large amount of alkali metal ions, and at least a part of the alkali metal cations are located on the silicon hydroxyl near the framework titanium in the form of counter cations, causing that the infrared spectrum characteristic absorption of the framework titanium appears in a range above 960 $cm^{-1}$ and below 980 $cm^{-1}$. The hydrothermal modification method of the alkali metal hydroxide solution provided by the present invention is essentially a modification method for the local environment of the framework titanium active site of the TS-1 zeolite. As far as we know, it has never been heard that the inhibition of side-reaction of hydrogen peroxide decomposition and promotion of the main reaction of hydrocarbons selective oxidations with hydrogen peroxide as the oxidant can be achieved at the same time by adjusting the local environment of the framework titanium active site of the titanium silicalite zeolite with alkali metal cations through a hydrothermal modification of the alkali metal hydroxide solution.

However, it should be indicated that the hydrothermal treatment modification method of the alkali metal hydroxide solution provided by the present invention is not effective for any TS-1 zeolite matrix. In brief, the present invention is suitable for the micron-sized TS-1 titanium silicalite zeolite or small-crystal TS-1 zeolite matrix synthesized by a non-classical method. Or more precisely, the present invention is applicable to larger crystal size TS-1 zeolites with a single crystal size more than 0.3 micron or preferably with a single crystal size more than 0.5 micron. We are surprised to find that the cheap TS-1 zeolite synthesized by the non-classical method has excellent catalytic performance for the gas phase epoxidation of propylene and hydrogen peroxide after being modified by the method of the present invention. In sharp contrast to this, nano TS-1 zeolite (the aggregate size is generally below 200-300 nanometers) synthesized by the classical method introduced by Taramasso et al. (U.S. Pat. No. 4,410,501. 1983) or Thangaraj et al. (J Chem Soc Chem Commun, 1992: 123) is not obviously improved in performance of the gas phase epoxidation of propylene and hydrogen peroxide after being modified by the hydrothermal method of the present invention. The reason for the difference is that the hydrothermal modification method of the alkali metal hydroxide solution provided by the present invention is fundamentally a dissolution modification, thus the TS-1 zeolite with too small crystal size is easy to be dissolved excessively or even thoroughly in the modification, so that the required alkali metal modified framework titanium active sites cannot be produced.

As described above, raw materials for the synthesis of TS-1 zeolite by the classical method have the features that the tetrapropylammonium hydroxide is used as the templating agent, and silicon ester and titanium ester are used as a silicon source and a titanium source, respectively. The morphology of the product observed on an electron microscope is characterized by irregular aggregates; the particle size of the aggregates is generally 200-300 nanometers; and the crystal size of the primary crystals which form the aggregates is generally below 100 nanometers. Although later people have done a lot of meaningful improvement work on the basis of Taramasso et al. and Thangaraj et al., the above basic features of TS-1 synthesized by the classical method are not changed and it is easy to judge. Because the cost of the raw materials of the classical method for synthesizing TS-1 is high, it is not bad that the present invention cannot be applied to the superfine TS-1 synthesized by the classical method.

Those skilled in the art know that the cheap TS-1 can be synthesized by different methods. For example, the following literature has reported the hydrothermal synthesis methods of the cheap TS-1: Zeolites and Related Microporous Materials: State of the Art 1994, Studies in Surface Science and Catalysis, Vol. 84; Zeolites 16: 108-117, 1996; Zeolites 19: 246-252, 1997; Applied Catalysis A: General 185 (1999) 11-18; Catalysis Today 74 (2002) 65-75; 1 Ind. Eng. Chem. Res. 2011, 50, 8485-8491; Microporous and Mesoporous Materials 162 (2012) 105-114; Chinese invention patents (application numbers) 201110295555.x and 201110295596.9. The raw materials of the cheap synthesis technology are characterized by using the tetrapropylammonium bromide as the templating agent, and using ammonium hydroxide or organic amines such as methylamine, ethylamine, ethylenediamine, diethylamine, n-butylamine and hexamethylenediamine as an alkali source. Silica sol and titanium tetrachloride are mainly used as the silicon source and the titanium source, and sometimes titanium ester is also used as the titanium source. The morphology of the product observed on the electron microscope is characterized by monodisperse crystals with regular crystal edges and planes, including large-grained thin plate crystals of several microns, or coffin-shaped small-grained crystals of 300-600 nanometers. For engineers familiar with the field, these characteristics are also easy to identify.

In fact, with regard to the application area of titanium silicalite zeolite matrix in the present invention, it is better not to define it with the terms of the classical synthesis method and the cheap synthesis method, but with the term of the crystal size of TS-1 zeolite. This is because the zeolite of titanium silicalite can also be synthesized by a gas-solid isomorphous substitution method, as described in the literature of Ind. Eng. Chem. Res. 2010, 49, 2194-2199. Therefore, it is emphasized herein that the fundamental requirement of the present invention for the TS-1 zeolite matrix is that the crystal size (referring to the single crystal rather than the aggregate) is at least ≥300 nanometers, and preferably ≥500 nanometers; the synthesis method belongs to the cheap method or not is not a matter. However, in view of the cost, the TS-1 zeolite hydrothermally synthesized by the cheap method may be a preferred option.

In addition to the crystal size, the present invention also requires the titanium silicalite matrix to have a relatively low silicon-titanium ratio and minimal non-framework titanium content. The two requirements are easy to be understood. Firstly, the gas phase epoxidation of propylene and hydrogen peroxide requires the zeolite of titanium silicalite to have high-density titanium active sites, which is beneficial to avoid the ineffective thermal decomposition of hydrogen peroxide. Secondly, as mentioned above, the hydrothermal modification method of the alkali metal hydroxide solution provided by the present invention is essentially a controlled dissolution modification method, does not have the function of recrystallizing the dissolved substances onto the zeolite framework, and certainly does not have the effect of recrystallizing the non-framework titanium species in the modified matrix onto the framework. Therefore, if the matrix of the titanium silicalite zeolite contains too much non-framework titanium species, even though the total silicon-titanium ratio seems appropriate, it is not conducive for the alkali metal ions modification to enrich the surface layer of the modified titanium silicalite zeolite with sufficient framework titanium active sites.

In addition, the present invention also requires the matrix of the titanium silicalite zeolite to have high enough relative crystallinity This is not difficult to understand. After all, the crystal framework is the support of the framework titanium.

The Present Invention has the Following Specific Implementation Solutions:

The fluidized reaction method for synthesizing propylene oxide by gas phase epoxidation of propylene and hydrogen peroxide is provided. The fluidized epoxidation is conducted at normal pressure and temperature above 100° C.; the raw materials of propylene and hydrogen peroxide are directly mixed in the gas phase; and the feed gas enables the catalyst to be fluidized in an epoxidation reactor. The catalyst is a microspherical catalyst formed with a kind of alkali metal ion modified titanium silicalite zeolite TS-1. The alkali metal ion modified titanium silicalite zeolite TS-1 has the characteristic that the alkali metal ions are reserved on the silicon hydroxyl of a modified TS-1 zeolite to modify the local environment of the framework titanium. Therefore, an infrared characteristic absorption band of framework titanium active site of the alkali metal ion modified titanium silicalite zeolite TS-1 appears in a range above 960 $cm^{-1}$ and below 980 $cm^{-1}$. The preparation steps of the catalyst are as follows:

Aft first step: preparing a TS-1 zeolite matrix. The TS-1 zeolite matrix shall meet the following technical requirements:

the size of the crystal size is preferably ≥0.3 micron, and more preferably ≥0.5 micron;
a silicon-titanium molar ratio composition is preferably ≤200, and more preferably ≤100;
the index value of the framework titanium content is preferably ≥0.4, and more preferably ≥0.45;
relative crystallinity is preferably ≥85%, and more preferably ≥90%.

The crystal size can be measured by a scanning electron microscope (SEM) or a transmission electron microscope (TEM). Those skilled in the art can obtain the electron microscope images of a TS-1 sample to be measured according to electron microscope sample preparation and experimental methods reported in any publication literature, and judge whether the crystal size of the TS-1 matrix meets the requirements according to the electron microscope images It should be noted that the crystal size in the present invention refers to the crystal size of the primary crystals (single crystals) of the TS-1, rather than the size of the aggregates of the TS-1 zeolite. The superfine TS-1 zeolite synthesized by the classical method often has agglomerate size close to or even larger than 0.3 micron (300 nanometers), but the crystal size of the primary crystals (single crystals) is often less than 0.1 micron (100 nanometers), so the superfine TS-1 zeolite is not suitable for use in the present invention. Those skilled in the art can judge the TS-1 particles on the electron microscope images are the single crystals or the aggregates according to the following experience: generally, the single crystals of the TS-1 zeolite have very regular coffin-shaped crystal morphology or thin plate-shaped crystal morphology, while the agglomerates of the superfine crystals of the TS-1 zeolite are often irregularly spherical.

The silicon-titanium molar ratio refers to the total average silicon-titanium ratio of bulk phase of the sample. X-ray fluorescence spectroscopy (XRF) can be used with reference sample to obtain silicon-titanium molar ratio data. Those skilled in the art can measure in person or entrust others to measure the silicon-titanium ratio data of the TS-1 matrix according to the instructions of an XRF instrument.

The index value of the framework titanium content is defined as $I_{960\ cm^{-1}}/I_{550\ cm^{-1}}$, that is, the ratio of the absorption peak intensity of Ti—O—Si antisymmetric stretching vibration characterized at 960 cm$^{-1}$ on the framework vibration infrared spectrum of the TS-1 zeolite to the absorption peak intensity of the five-membered ring vibration of MFI structure characterized at 550 cm$^{-1}$. Those skilled in the art know that the ratio has been generally accepted by researchers in the field and used to reflect the relative amount of the framework titanium in the TS-1 zeolite (for example, CATAL. REV.-SCI. ENG., 39(3). 209-251 (1997) uses the value of $I_{960\ cm^{-1}}/I_{550\ cm^{-1}}$ to give the correlation diagram P217 FIG. 4b). The larger the value of $I_{960\ cm^{-1}}/I_{550\ cm^{-1}}$ is, the higher the content of the framework titanium in the TS-1 framework is. Those skilled in the art can refer to experimental method of the infrared vibration spectroscopy of the titanium silicalite zeolite framework introduced by any publication literature to obtain the value of $I_{960\ cm^{-1}}/I_{550\ cm^{-1}}$. The present invention provides the following practice for reference: pre-drying the spectral purity KBr at 110° C. for 4 hours, then mixing and grinding KBr and the TS-1 into a powder at a ratio of 100 to 200:1, pressing the powder into a wafer at a pressure of 6 MPa, and putting the wafer into an infrared sample cell for testing. The peak intensity of the two absorption peaks at 960 cm$^{-1}$ and 550 cm$^{-1}$ can be directly read from the spectrum with the software of a spectrometer, so that the value of $I_{960\ cm^{-1}}/I_{550\ cm^{-1}}$ can be conveniently calculated.

The relative crystallinity refers to the ratio (expressed by percentage) of the sum of the intensity of five characteristic diffraction peaks (2θ=7.8°, 8.8°, 23.0°, 23.9° and 24.3°) of the TS-1 zeolite matrix measured by the X-ray powder diffraction method (XRD) to that of a reference sample. Those skilled in the art can obtain the XRD patterns of the TS-1 zeolite matrix and the reference sample according to the XRD experimental methods reported in any publication literature. The present invention recommends using embodiment 1 in the Chinese invention patent (application number) 201110295555.x to prepare the reference sample. Specifically: 220 ml of deionized water is added to 225 g of silica sol (20% wt); after stirring for 10 minutes, 18.4 g of tetrapropylammonium bromide and 5.1 g seed crystals are added to the diluted silica sol; after continuing stirring for 20 minutes, a silicon solution is obtained; tetrabutyl titanate and acetylacetone are mixed at a mass ratio of 1:0.8, and stirred for 15 minutes to prepare a titanium solution; 19.7 ml of the prepared titanium solution is added to the silicon solution; after stirring for 30 minutes, 57 ml of n-butylamine is added and continuously stirred for 15 minutes to obtain uniform gel; then 6.0 g of $Na_2SO_4$ is added and stirred for 10 minutes; then the obtained gel is added to a 2 l stainless steel autoclave and crystallized under autogenous pressure and 170° C. for 24 hours; after crystallization the product is filtered, washed to be neutral, and dried at 110° C. It is emphasized herein that before measuring the XRD patterns of the TS-1 matrix and the reference samples, the two samples to be measured must be calcined to ensure that the organic templating agents in the samples are removed completely and more than 95%, preferably more than 98% of dry basis content of the zeolite is achieved. Thus, it is recommended to dry about 2 g of TS-1 matrix and about 2 g of reference samples overnight at 110° C., and then place the samples in a muffle furnace for temperature-programmed calcination. The temperature-programmed calcination starts at room temperature, and the temperature is raised to 300° C. at a temperature rise rate of 10° C./min, and then the temperature is raised from 300° C. to 500° C. at a temperature rise rate of 1° C./min and kept constant until the sample is completely white.

The TS-1 zeolite which meets the above indexes can be used as the modified matrix of the present invention. The TS-1 zeolite suitable for the present invention can be purchased from the market, or can be synthesized by engineers familiar with the field according to the relevant publication literature and patent documents. If the TS-1 zeolite is synthesized by the engineers, the present invention recommends adopting the hydrothermal synthesis method of the TS-1 reported in the following publication literature and patent documents: Zeolites and Related Microporous Materials: State of the Art 1994, Studies in Surface Science and Catalysis, Vol. 84; Zeolites 16: 108-117, 1996; Zeolites 19: 246-252, 1997; Applied Catalysis A: General 185 (1999) 11-18; Catalysis Today 74 (2002) 65-75; 1 Ind. Eng. Chem. Res. 2011, 50, 8485-8491; Microporous and Mesoporous Materials 162 (2012) 105-114; Chinese invention patents (application numbers) 201110295555.x and 201110295596.9.

The organic templating agent of a qualified TS-1 zeolite matrix must be removed before modification. It is the common knowledge in the art to remove the organic templating agent from a zeolite. The present invention provides the following reference practice: drying an appropriate amount of TS-1 zeolite matrix overnight at 110° C., and then placing the sample in the muffle furnace for temperature-programmed calcination. The temperature-programmed calcination starts at room temperature, and the temperature is raised to 300° C. at a temperature rise rate of 5° C./min, and then the temperature is raised from 300° C. to 400° C. at a temperature rise rate of 1° C./min and kept constant for 12 hours; then the temperature is raised to 450° C. at the same temperature rise rate and kept constant for 12 hours; and finally, the temperature is raised to 500° C. at the same temperature rise rate and kept constant until the sample is completely white.

At second step: preparing an alkali metal hydroxide modification solution. In order to achieve the effect of degree controlled hydrothermal modification, the present invention requires that:

The preferred range of the concentration of the alkali metal hydroxide solution is: a lower limit of 0.05 mol/L and an upper limit of 0.2 mol/L (calibrated at room temperature), and a more preferred range is: the lower limit of 0.08 mol/L and the upper limit of 0.15 mol/L (calibrated at room temperature).

The alkali metal hydroxide is preferably lithium hydroxide, sodium hydroxide and potassium hydroxide; and more preferably sodium hydroxide and potassium hydroxide.

When the modification solution is prepared, any one of the alkali metal hydroxides recommended above can be used alone, or a mixture of any two of the alkali metal hydroxides in any ratio can be used, or a mixture of three hydroxides in any ratio can also be used. When more than two alkali metal hydroxides are used to prepare the modification solution, the solution concentration refers to the sum of the molar concentrations of various hydroxides.

Considering that commercially available alkali metal hydroxides contain a certain amount of impurities, the purity of the raw materials of the alkali metal hydroxides should be analyzed by chemical titration before the modification solution is prepared. Those skilled in the art can perform the titration operation according to a conventional chemical analysis method. Similarly, after the modification solution is prepared, the same conventional chemical analysis method should be used to calibrate the hydroxide concentration of the modification solution. Because the alkali metal hydroxides release a large amount of heat in the dissolution process, the concentration is calibrated only when the solution is cooled to room temperature.

During modification, the concentration of the alkali metal hydroxide in the modification solution will decrease as a result of the reaction of the alkali solution with the zeolite framework (for example, $NaOH+Si-OH=Si-O^- Na^+ + H_2O$). Meanwhile, the used alkali metal hydroxide solution will also contain low concentrations of silicate, titanate and silicotitanate due to the framework dissolution and desilication reaction (a small amount of framework titanium is inevitably dissolved in the process). However, undoubtedly, the used alkali metal hydroxide solution can be recycled conditionally, which can reduce the modification cost and waste solution discharge. Before the used solution is recycled, the concentration of the alkali metal hydroxide needs to be accurately measured in order to restore the initial concentration by supplementing the alkali metal hydroxide; and the concentrations of the silicate, the titanate and the silicotitanate contained in the solution also need to be measured in order to control the number of cycles. In order to avoid too complicated and lengthy description of the present invention and to make it easier for the colleagues to understand the gist of the present invention, the present invention will not provide detailed illustration for the recycling of the used modification solution herein and in subsequent embodiments. The engineers in the art can recycle the used modification solution according to the common sense.

However, it should be stated that, just as the used modification solution can be recycled, it is beneficial that a certain amount of alkali metal silicate, titanate and titanium silicate is added deliberately into the fresh modification solution in order to control the degree of dissolution modification. We have even found that the introduction of suitable amount of alkali metal carbonate and bicarbonate into the fresh modification solution can also assist in controlling the degree of dissolution modification. The commonality of the above salts is that they belong to strong alkali and weak acid salts, and can be hydrolyzed in the aqueous solution to provide alkali metal cations and hydroxyl anions, that is, alkali metal hydroxides are actually produced by hydrolysis. The difference from the direct addition of the alkali metal hydroxides is that the weak acid salt produces weak acid after hydrolysis, which can adjust the pH value of the modification solution to a certain extent, thereby helping to control the degree of dissolution modification. In terms of the strong alkali and weak acid salts, alkali metal phosphates and hydrogen phosphates should also be candidates, but the phosphates and the hydrogen phosphates are easy to accumulate in the recycling of the modification solution, which is not conducive to multiple recycling of the modified solution. The engineers familiar with the field can select and use other strong alkali and weak acid salts with alkali metal under the guidance of the above principles described in the present invention, and the principles will not be repeated.

At third step: conducting degree controlled hydrothermal treatment on the TS-1 zeolite matrix by using the alkali metal hydroxide solution. The hydrothermal treatment can be conducted under static and stirring states. In order to achieve the effect of degree controlled hydrothermal treatment, the present invention requires that:

The preferred ratio range of volume of the modification solution to weight of the titanium silicalite zeolite matrix is from the lower limit of 5 ml/g to the upper limit of 15 ml/g, and a more preferably ratio range is from the lower limit of 8 mug to the upper limit of 12 mug.

The preferred range of the hydrothermal modification temperature is from the lower limit of 100° C. to the upper limit of 200° C., and a more preferred range is from the lower limit of 150° C. to the upper limit of 190° C.

The preferable range of the hydrothermal modification time is from the lower limit of 10 hours to the upper limit of 20 hours, and a more preferable range is from the lower limit of 15 hours to the upper limit of 20 hours.

It should be specially explained that, in order to achieve the effect of degree controlled hydrothermal treatment, all the parameters such as the concentration of the alkali metal hydroxide modification solution, the ratio of volume of the modification solution to weight of the titanium silicalite zeolite matrix, the modification temperature and time need to be taken into consideration together. It is not difficult for those skilled in the art to understand that the lower limit values of all the hydrothermal modification parameters involved in the second step and the third step can produce the weakest degree of dissolution modification effect, and the upper limit values of all the hydrothermal modification parameters can produce the strongest degree of dissolution modification effect. Therefore, the modification conditions defined by the combination of the lower limit values of all the parameters inevitably generate the lowest degree of dissolution modification result, and the modification conditions defined by the combination of the upper limit values of all the parameters inevitably generate the highest degree of dissolution modification result. Therefore, it is not difficult to understand that the hydrothermal modification result between the lowest degree and the highest degree will be obtained by selecting the lower limit value of a certain parameter and the intermediate values and the upper limit values of other parameters. Of course, it is not difficult to understand that the modification conditions formed by the combination of different values of various parameters can generate different degrees of hydrothermal modification results. When the values of the parameters are designed for a given titanium silicalite zeolite matrix to reach a desired modification degree which guarantees a satisfactory catalytic performance in the gas phase epoxidation of propylene and hydrogen peroxide, it is the exact meaning of the degree controlled hydrothermal modification in the present invention. Clearly, the lowest degree of dissolution modification effect and the highest degree of dissolution modification effect herein shall not be mistakenly understood as the worst modification effect and the best modification effect. Some titanium silicalite zeolite matrices need the lowest degree of hydrothermal dissolution modification, while some other titanium silicalite zeolite matrices need higher degree of hydrothermal dissolution modification. Therefore, the present invention clarifies that the combination conditions for the hydrothermal modification for a specific titanium silicalite zeolite matrix should be determined through experiments, and shall be judged based on the position of the infrared vibration absorption peak of the active site, especially based on the gas phase epoxidation data of propylene and hydrogen peroxide.

The engineers in the field can determine specific modification conditions suitable for the specified titanium silicalite zeolite within the parameter value range recommended by the present invention according to specific considerations such as equipment use efficiency, modification cost and wastewater discharge.

At fourth step: conducting post-treatment on the hydrothermally modified TS-1 zeolite. Specifically, the step comprises conventional solid-liquid separation, washing, drying and calcining steps. However, for the present invention, correct washing of the wet material of the zeolite after solid-liquid separation is the key. The present invention recommends using a low-concentration alkali metal hydroxide solution to wash the wet material of the modified zeolite obtained by solid-liquid separation, and the degree of washing is satisfactory when no precipitate appears after the washing solution is neutralized with acid. The present invention requires that the preferred range of the concentration of the alkali metal hydroxide solution used for the washing purpose is from the lower limit of 0.001 mol/l to the upper limit of 0.05 mol/l (calibrated at room temperature), and successive preferred ranges are from the lower limit of 0.005 mol/l to the upper limit of 0.04 mol/l, from the lower limit of 0.005 mol/l to the upper limit of 0.03 mol/l and from the lower limit of 0.005 mol/l to the upper limit of 0.01 mol/l (calibrated at room temperature). The alkali metal hydroxide is preferably lithium hydroxide, sodium hydroxide and potassium hydroxide; and more preferably sodium hydroxide and potassium hydroxide.

The necessity of washing is that, on one hand, the wet material of the zeolite obtained from solid-liquid separation still has a considerable amount of residual used modification solution existed in the form of a surface liquid film and capillary condensate, roughly account for 40-50 wt. % of the weight of the wet material. The residual used modification solution mainly contains free alkali metal hydroxides, it also contains silicate ions, titanate ions and titanium silicate ions and larger zeolite framework fragments dissolved from the zeolite framework. The free alkali may continue to react with the silicon hydroxyl in the drying process and destroy an expected modification degree, while other species may become blockages of the porous channels of the zeolite and even become the active sites that cause various side-reactions. On the other hand, improper washing method and degree may easily lead to the loss of useful alkali metal ions balanced on the silicon hydroxyl. Therefore, it is very important to select correct washing method and degree. The alkali metal hydroxide solution used for the washing purpose in the present invention is an alkali metal hydroxide solution having a concentration much lower than that of the modified solution. The simplest practice is to use a lower-concentration alkali metal hydroxide solution with the same type as the modification solution as the washing solution. The present invention provides the following reasons for selecting the alkali metal hydroxide as the washing solution: firstly, the use of the alkali metal hydroxide solution as the washing solution is beneficial to supplement the lost of useful alkali metal ions balanced on the silicon hydroxyls in the washing process. Secondly, the alkali metal hydroxide solution is strongly alkaline The fall off and runoff of the useful alkali metal ions balanced on the silicon hydroxyl can be prevented by maintaining the strong alkalinity of the washing solution in the washing process. Otherwise, if deionized water is selected as the washing solution, the useful alkali metal ions balanced on the silicon hydroxyl are easy to lose in the form of NaOH due to the reverse reaction of $NaOH+Si-OH=Si-O^-+H_2O$. That is, the hydrolysis reaction of strong alkali and weak acid salt ($Si-O^-\ Na^+$). This is exactly the reason that the existing patents involving inorganic base modification can remove the alkali metal ions in the washing step. Therefore, in order to obtain the alkali metal ion modified TS-1 zeolite, the deionized water is not suitable for the present invention, and a solution with an acidic pH value also cannot be used as the washing solution for the wet material after solid-liquid separation. The reason is self-evident.

Of course, it is entirely feasible in principle, but is not desirable from the perspective of environmental protection and cost that low-concentration quaternary ammonium alkali solutions or other organic alkali aqueous solutions with strong alkalinity are used as the washing solution.

In addition, the purpose of the present invention emphasizing the use of the alkali metal hydroxide solution with a concentration lower than that of the modification solution as the washing solution, is to reduce the residual amount of free alkali metal hydroxide in the modified TS-1 after washing. The shortcomings of excessive free alkali metal hydroxide remaining in the modified TS-1 has been explained above.

The simplest applicable way for the solid-liquid separation in the present invention comprises centrifugation and filtration. However, when centrifugation and filtration modes are used, it is preferably not to introduce additives such as flocculants and filter aids to prevent the pH value of the solution from changing or even causing the precipitate. Other solid-liquid separation modes are allowed to be used as long as obvious liquid phase concentration, precipitation of precipitates and pH change are not caused in the separation process.

The drying and calcining in the present invention can be conducted in an air atmosphere according to conventional practices. The reference practice recommended by the present invention is as follows: the drying temperature range is 80-120° C., and the drying time is decided based on the dry basis content of the sample not less than 90%. The recommended final calcining temperature range is 400-550° C., and the constant temperature time at the final temperature is not less than 3 hours.

The implementation effects of conducting degree controlled hydrothermal treatment on the titanium silicalite zeolite TS-1 by using the alkali metal hydroxide solution as described above can be evaluated by the following method.

Firstly, infrared spectroscopy is used to characterize the absorption peak position of the framework titanium active site of the modified TS-1 zeolite. The method comprises: putting an appropriate amount of sample from the modified TS-1 zeolite treated by the fourth step into a small beaker, putting an appropriate amount of spectral purity KBr into another small beaker, and putting the two small beakers into an oven at 110° C. simultaneously for pre-drying for 4 hours; then mixing and grinding KBr and TS-1 into powder at a ratio of 200:1, and pressing into a wafer under a pressure of 6 MPa; putting the wafer into an infrared sample cell for testing to obtain an infrared spectrum; and finally, using the second derivative spectrum in the infrared software to accurately locate the infrared characteristic absorption peak position of the framework titanium active site modified by the alkali metal ions.

Secondly, the X-ray fluorescence spectroscopy (XRF) method is used to obtain the silicon-titanium molar ratio and sodium ion content data of the modified sample.

In addition, a small fixed bed reactor is used to evaluate the gas phase epoxidation performance of the modified TS-1 zeolite. It is recommended to refer to the experimental devices and methods described in the previously published journal papers and authorized Chinese invention patents to evaluate the gas phase epoxidation of propylene and hydrogen peroxide. References recommended by the present invention include: Chem. Commun., 2005, 1631-1633; Modern Chemical Industry, Vol. 26 Supplement, 2006, P194-197; AIChE J, 53: 3204-3209, 2007; Advanced Technology of Electrical Engineering and Energy, Vol 28, 2009, No. 3, P73-76; Chin. J. Catal., 2010, 31: 1195-1199; CIESC Journal Vol 63, 2012, No. 11, P3513-3518; Journal of Catalysis 288 (2012) 1-7; Angew. Chem. Int. Ed. 2013, 52, 8446-8449; AIChE J, 64: 981-992, 2018; Chinese invention patents (application numbers) 200310105210.9, 200310105211.3 and 200310105212.8.

The characteristic of the evaluation method is the use of the integrated reactor. The upper segment of the integrated reactor is a self-cooling dielectric barrier discharge reactor for in-situ synthesis of gaseous hydrogen peroxide from hydrogen and oxygen plasma. The lower segment of the integrated reactor is a conventional fixed bed reactor which contains titanium silicalite zeolite particles (20-40 meshes) for the gas phase epoxidation of propylene and hydrogen peroxide. The working principle of the integrated reactor is: hydrogen and oxygen are mixed at 170 ml/min and 8 ml/min respectively under the control of a mass flow controller, and then enter the self-cooling dielectric barrier discharge reactor in the upper segment of the integrated reactor to synthesize gaseous hydrogen peroxide. The yield of hydrogen peroxide can reach 0.35 g/h. The synthesized hydrogen peroxide gas is carried by excess hydrogen to enter the epoxidation reactor in the lower segment from a gas hole between the two segments of reactors, and is fully mixed with propylene gas (18 ml/min) which enters the segment of reactor from a side line to jointly enter the TS-1 catalyst bed for conducting the epoxidation.

The reaction conditions are: the loading of the TS-1 catalyst is 0.5 g (the catalyst powder is tableted and then crushed and sieved to obtain 20-40 meshes); the actual molar ratio of propylene to hydrogen peroxide is about 5:1; and the gas phase epoxidation is conducted at atmospheric pressure and 130° C.

At Fifth step: processing the alkali metal ion modified titanium silicalite zeolite TS-1 into a microspherical catalyst by a spray forming method.

The spray forming can be conducted by the conventional methods. The present invention provides the following recommendations:

(1) The suspension of the modified TS-1 zeolite is prepared with the acidic hydrolysis solution of tetraethyl orthosilicate. About 6 kg of tetraethyl orthosilicate is added to 5-6 kg of deionized water under stirring. Then, concentrated nitric acid is dropwise added to the solution to hydrolyze the estersil at room temperature under acidic conditions, the alcohol formed is distilled (at temperature of 55-60° C.) to obtain a binder glue solution. Next, an appropriate amount of alkali metal ion modified TS-1 zeolite is dispersed in the binder glue solution, and the dispersion liquid is treated with a colloid mill to make the particle size $D_{90}$ of particulate matter less than or equal to 8 microns, thereby obtaining a zeolite suspension for spray forming.

The preferred acidity value of the estersil hydrolyzed at room temperature under the acidic conditions is pH=3.0-4.0.

The total solid content (TS-1 zeolite and silicon oxide) in the zeolite suspension is preferably 20-35 wt %.

The ratio of the zeolite to the solid content in the zeolite suspension is preferably 40-80 wt %, and more preferably 50-70 wt %.

(2) The spray forming is conducted with a spray drying tower. The temperature of hot air entering the tower is 350° C., and the temperature of exhaust air exiting the tower is not less than 100° C.

(3) The spray forming product collected from the spray drying tower are subjected to conventional drying and calcining treatment to obtain the microspherical TS-1 catalyst product. Drying can be conducted at 110° C. until the dry basis content is not less than 90 wt %. Calcining can be conducted at a temperature of 540-600° C., and the recommended calcining time is 1-10 hours.

In the step, a laser particle size distribution analyzer can be used to analyze and measure the particle size distribution of the spray forming catalyst product after calcining, and a scanning electron microscope (SEM) is used to observe the sphericity of the microspherical catalyst product.

The gas phase epoxidation of propylene and hydrogen peroxide is conducted using a fluidized reactor.

A simple small bubbling bed reaction device is used for example. The reaction device is composed of propylene feed, hydrogen peroxide feed, propylene raw material preheating, reactor and reactor heating, online gas chromatography analysis, and the like. The structure of the reactor and the working principle of the reaction device are shown in FIG. 8 and FIG. 9. The specific experimental method is as follows:

Firstly, the weighed microspherical alkali metal ion modified TS-1 catalyst is loaded into the reactor, and then the reactor is installed on the reaction device. The feed amount of propylene feed gas is controlled by a mass flowmeter, and the feed amount of hydrogen peroxide solution is controlled by a peristaltic pump. Hydrogen peroxide solution comes into contact with propylene feed gas before entering the reactor, and is fully vaporized in the process. Thus, propylene feed gas shall be preheated by a propylene feed preheater before coming into contact with hydrogen peroxide solution. In order to adjust the fluidized state of the catalyst, nitrogen is used as the diluent gas of propylene in the experiment. The nitrogen flow is controlled by the mass flowmeter. The nitrogen and propylene feed gas are mixed before the preheater. When hydrogen peroxide solution comes into contact with the preheated mixture of propylene and the nitrogen, hydrogen peroxide solution is instantly vaporized, then enters the bottom of the reactor together with the mixture of propylene and the nitrogen, and then penetrates through a quartz sieve plate distributor to come into contact with the microspherical alkali metal ion modified TS-1 catalyst to carry out a gas-solid phase fluidized propylene epoxidation. The bottom space of the reactor and the quartz sieve plate distributor provide sufficient mixing conditions for propylene and hydrogen peroxide gas. During the gas-solid phase fluidized epoxidation of propylene and hydrogen peroxide gas, the molar ratio of propylene and hydrogen peroxide and the heater temperature of the reactor are unchanged, and reaction products and the conversion rate of propylene are quantitatively analyzed by online gas chromatography. Because hydrogen peroxide that fails to take part in the epoxidation is finally thermally decomposed at the temperature of the gas phase epoxidation, the conversion rate of hydrogen peroxide is not analyzed and calculated in the experiment.

The present invention has the following beneficial effects:

(1) The present invention uses the gas-solid phase fluidized bed reaction mode for the epoxidation of propylene and hydrogen peroxide to synthesize propylene oxide for the first time. The superiorities at least include: the present invention is beneficial to inhibit the self-decomposition side-reaction of hydrogen peroxide, beneficial to disperse the reaction heat and rapidly take away the heat, beneficial to improve the utilization rate of the catalyst and the production capacity of the unit catalyst, and beneficial to industrial application and industrial production safety.

(2) The present invention uses the alkali metal hydroxide solution to conduct degree controlled hydrothermal treatment on the TS-1 zeolite for the first time. The modified TS-1 zeolite contains a large amount of alkali metal ions, and at least a part of the alkali metal cations are located on the silicon hydroxyl near the framework titanium in the form of counter cations, to regulate the local environment of the framework titanium active site of the titanium silicalite zeolite, causing that the infrared spectrum characteristic absorption of the framework titanium appears in a range above 960 cm' and below 980 cm'. The alkali metal ion modified framework titanium active site can obviously inhibit the self-decomposition side-reaction of hydrogen peroxide at high temperature in a normal propylene/hydrogen peroxide feed ratio, thereby increasing the conversion rate of propylene in the gas phase epoxidation, reducing the generation of oxygen, increasing the utilization rate of hydrogen peroxide and improving the economy and the safety of the reaction.

DETAILED DESCRIPTION

Figure 1:
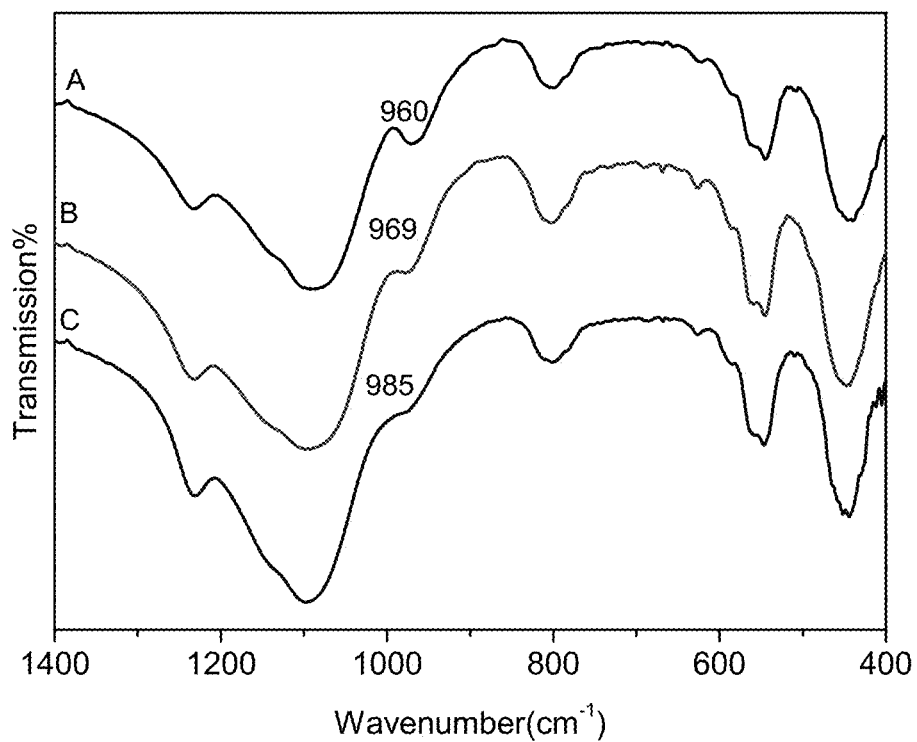
FIG. 1 shows the framework vibration FT-IR spectra of catalyst samples of embodiment 1 and reference embodiment 2.

The following embodiments only serve to further illustrate the present invention, but shall not be used to limit the contents of the present invention. The reagents and drugs involved in all the embodiments are commercially available and analytically pure.

The SEM images are obtained with the NOVA NanoSEM 450 field emission scanning electron microscope from American FbI Company. The voltage is 230 kV, the frequency is 60 Hz, the current is 8 A, and the magnification is 800,000 to 1,600,000. Samples are dispersed into anhydrous alcohol, and dripped on silicon wafers with a capillary. Then, after fixed on the conductive adhesive, the samples are subjected to metal spraying treatment and the image is observed.

X-ray fluorescence spectroscopy (XRF) composition analysis: a German Bruker S8 Tiger X-ray fluorescence spectrometer is used; 1.2 g of TS-1 sample is uniformly mixed with 4 g of boric acid to prepare tablets; and a standard-sample-free method is used for measurement.

Framework vibration characterization of FT-IR spectrum TS-1: characterization is carried out on the IS10 infrared spectrometer of Nicolet company; KBr is used for tabletting; the range of the scanning wave number is 4000-400 $cm^{-1}$; and the scanning frequency is 64.

X-ray powder diffraction (XRD) crystal structure analysis: D/max·2400 X-ray powder diffractometer from Japanese Rigaku company is used for measurement; CuKα radiation is adopted; the voltage is 40 kV; the current is 100 mA; the range of the scanning diffraction angle is 2θ=4–40°; the scanning speed is 2°/min; and the scanning stride is 0.08°. The relative crystallinity is obtained according to the ratio of the sum of the peak intensities of five MFI structural characteristic peaks at 2θ=7.8°, 8.8°, 23.2°, 23.8° and 24.3° in the XRD spectrum and the sum of the intensities of five diffraction peaks (selected) of the reference sample.

Laser particle size distribution analysis is conducted on a Bettersize2000 laser particle size distribution analyzer made in China The Bettersize2000 laser particle analyzer is an intelligent laser particle analyzer using a single-beam dual-lens technology, has a test range of 0.02-2000 μm, and has special functions such as automatic test, automatic light path calibration (automatic centering), automatic water intake, automatic drainage, automatic bubble elimination, automatic washing, automatic printing and automatic saving. All the operations are automatically completed under the control of a computer. Experimenters can perform analysis and determination according to the operation manual Embodiment 1. The present embodiment is used to illustrate that the large-crystal micron-sized TS-1 zeolite modified by the degree controlled hydrothermal treatment method of the alkali metal hydroxide solution provided by the present invention, evaluated on a small fixed bed reactor after tableted, exhibits high activity and selectivity and utilization rate of hydrogen peroxide for the gas phase epoxidation of propylene and hydrogen peroxide.

At first step: synthesizing and preparing the large-crystal micron-sized TS-1 zeolite matrix according to the method introduced in Appl. Catal. A, 185, (1999) 11-18.

The specific feed amount and synthesis steps are as follows:

220 ml of deionized water is added to 225 g of silica sol (26% wt); after stirring for 10 minutes, 18.4 g of tetrapropylammonium bromide is added to the diluted silica sol solution; after continuing stirring for 20 minutes, a silicon solution is obtained; tetrabutyl titanate and acetylacetone are mixed at a mass ratio of 1:0.8, and stirred for 15 minutes to prepare a titanium solution; 19.7 ml of the titanium solution is added to the silicon solution; after stirring for 30 minutes, 57 ml of n-butylamine is added and continuously stirred for 15 minutes to obtain uniform gel; then the obtained gel is added to a 2 l stainless steel autoclave and the hydrothermal synthesis is carried out at 170° C. for 96 hours under agitation. After the crystallization time is reached, the hydrothermal crystallization autoclave is naturally cooled to room temperature at first, then the autoclave is opened, and the mother solution is removed by Buchner funnel suction filtration to obtain a zeolite filter cake. The filter cake is washed with deionized water for several times until the pH value of the washing solution is close to 7.0. Then, the filter cake is put into an electric oven and dried overnight at 110° C. The dried solid is then transferred into a muffle furnace for temperature-programmed calcination to remove the templating agent. The temperature-programmed calcination starts at room temperature, and the temperature is raised to 300° C. at a temperature rise rate of 10° C./min, and then the temperature is raised from 300° C. to 500° C. at a temperature rise rate of 1° C./min and kept constant until the sample is completely white, so as to obtain the large-crystal micron-sized TS-1 zeolite matrix.

In order to use a reference sample to calculate the relative crystallinity of the large-crystal micron-sized TS-1 zeolite matrix, embodiment 1 in the Chinese invention patent (application number) 201110295555.x is used to prepare the reference sample. Specifically: 220 ml of deionized water is added to 225 g of silica sol (20% wt); after stirring for 10 minutes, 18.4 g of tetrapropylammonium bromide and 5.1 g of seed crystals are added to the diluted silica sol solution; after continuing stirring for 20 minutes, a silicon solution is obtained; tetrabutyl titanate and acetylacetone are mixed at a mass ratio of 1:0.8, and stirred for 15 minutes to prepare a titanium solution; 19.7 ml of the titanium solution is added to the silicon solution; after stirring for 30 minutes, 57 ml of n-butylamine is added and continuously stirred for 15 minutes to obtain uniform gel; then 6.0 g of $Na_2SO_4$ is added and stirred for 10 minutes; and then the obtained gel is added to a 2 l stainless steel autoclave and crystallized at 170° C. for 24 hours under agitation. The post-treatment method of the reference sample is conducted by referring to the processing method of the large-crystal micron-sized TS-1 zeolite matrix.

SEM, XRF, FT-IR and XRD are used to characterize the crystal size of the large-crystal micron-size TS-1 zeolite matrix. Results show that the crystal size is 1×2×6 μm, the total Si/Ti molar ratio is about 39.8, and the sodium-titanium molar ratio is 0.003. The index value $I_{960\ cm-1}/I_{550\ cm-1}$ of the framework titanium content is about 0.51 and the relative crystallinity is about 100%. The measurement results show that the synthesized large-crystal micron TS-1 matrix meets the requirements of the present invention.

At second step: preparing 0.1 mol/L sodium hydroxide modification solution.

The solution is prepared with analytically pure sodium hydroxide solid particles (96%) and deionized water. Firstly, 4.17 g of solid sodium hydroxide particles is accurately weighed. Then, a 1 l volumetric flask is used to prepare a 0.1 mol/L sodium hydroxide solution (cooled to room temperature). For the sake of caution, a standard reagent potassium hydrogen phthalate and a phenolphthale indicator are used to calibrate the prepared sodium hydroxide solution in accordance with conventional operation. A qualified solution has a relative deviation of the concentration value of less than 5%. Otherwise, the modified solution is prepared again.

At third step: using 0.1 mol/L sodium hydroxide solution to conduct the degree controlled hydrothermal treatment on the large-crystal micron-sized TS-1 zeolite matrix.

Specifically, 70 ml of the calibrated 0.1 mol/L sodium hydroxide solution is accurately measured with a measuring cylinder and added to a plastic cup with magnetic stirrer. Then, 7 g of the large-crystal micron-sized TS-1 zeolite matrix that is calcined in the first step is weighed, and slowly added into the sodium hydroxide solution under agitation. After the large-crystal micron-sized TS-1 zeolite matrix is completely added to the solution, the stirring speed is appropriately increased to make the slurry to a uniform state. The stirring is continued for 2 hours at room temperature, and then stopped; and the slurry is transferred into a 100 ml hydrothermal autoclave and sealed. The hydrothermal autoclave is heated in an oven of 170° C. for 18 hours at constant temperature.

At fourth step: conducting post-treatment on the modified TS-1 zeolite.

After the hydrothermal treatment is ended, the hydrothermal autoclave is taken out of the electric oven and quickly cooled to room temperature with tap water. Then the hydrothermal autoclave is carefully opened, and the mother solution is removed by Buchner funnel suction filtration to obtain a zeolite filter cake. The filter cake is washed with 0.01 mol/L sodium hydroxide solution until no precipitate appears after the filtrate is neutralized with acid. Then, the filter cake is put into the electric oven and dried overnight at 110° C. to ensure that the dry basis content of the solid powder (solid content measured after calcining at 500° C. for 3 hours) is not less than 90%. Finally, the dried solid powder is calcined at a constant temperature of 540° C. for 6 hours to obtain the modified product of embodiment 1.

The sodium ion modified TS-1 zeolite prepared in the present embodiment is tested and evaluated as below:

Firstly, infrared spectroscopy is used to characterize the absorption peak position of the framework titanium of the modified TS-1 zeolite.

An appropriate amount of the modified product in the fourth step is put into a small beaker; an appropriate amount of spectral purity KBr is put into another small beaker; and the two small beakers are simultaneously put into the oven at 110° C. for pre-drying for 4 hours. Then KBr and the modified TS-1 product are mixed and ground at a ratio of 200:1, and pressed into a wafer under a pressure of 6 MPa; the wafer is put into an infrared sample cell for testing to obtain an infrared spectrum; and finally, the second derivative spectrum in the infrared software is used to accurately locate the infrared characteristic absorption peak position of the framework titanium active site modified by the alkali metal ions, which is at 969 $cm^{-1}$ for the modified zeolite product of embodiment 1.

In addition, the X-ray fluorescence spectroscopy (XRF) method mentioned in the first step is used to obtain the silicon-titanium molar ratio and sodium-titanium molar ratio of the modified zeolite product of embodiment 1, which are 37.6 and 0.86, respectively.

The characterization results of the infrared spectroscopy and the X-ray fluorescence spectroscopy show that the hydrothermal treatment of the large-crystal micron-sized TS-1 zeolite matrix with 0.1 mol/L sodium hydroxide solution produces a controllable silicon dissolution effect, so that the silicon-titanium molar ratio of the modified zeolite is slightly lower than that of the matrix. At the same time, a large amount of sodium ions exist in the modified zeolite, which makes that the infrared characteristic absorption peak of the framework titanium active site shifted from 960 cm$^{-1}$ (matrix, FIG. 1A) to 969 cm$^{-1}$ (FIG. 1B). Namely, in the process of degree controlled hydrothermal treatment modification for the large-crystal micron-sized TS-1 zeolite matrix with 0.1 mol/L sodium hydroxide solution, the sodium ions replace the hydrogen protons on the silicon hydroxyl near the framework titanium in the form of counter cations, and therefore change the local environment of the nearby framework titanium site.

Then, a small fixed bed reactor is used to evaluate propylene gas phase epoxidation performance of the sodium ion modified TS-1 zeolite.

The integrated reactor reported in Chin. J. Catal., 2010, 31: 1195-119 is used for a gas phase epoxidation experiment. The upper segment of the reactor is a self-cooling dielectric barrier discharge reactor for in-situ synthesis of gaseous hydrogen peroxide from hydrogen and oxygen plasma. The lower segment of the integrated reactor is a conventional fixed bed reactor which contains titanium silicalite zeolite particles (20-40 meshes) for the gas phase epoxidation of propylene and hydrogen peroxide. Specific operation steps are as follows: (1) the yield of hydrogen peroxide is calibrated with the upper segment of plasma reactor: at this moment, the lower segment of reactor should be removed. Firstly, the self-cooling circulating water of the upper segment of reactor is opened. Then, a hydrogen cylinder and the mass flow controller are started to control the hydrogen flow to be 170 ml/min; and next, the oxygen cylinder and the mass flow controller are started to slowly increase the oxygen flow to be 8 ml/min. During the discharge reaction of the upper segment of reactor, the flows of the hydrogen and the oxygen should be accurately controlled and the hydrogen and the oxygen should be mixed uniformly before entering the upper segment of reactor. Then, dielectric barrier discharge is performed according to the discharge methods introduced in Chinese invention patents (application numbers) 200310105210.9, 200310105211.3 and 200310105212.8, so that the hydrogen-oxygen mixture entering the self-cooling dielectric barrier discharge reactor at the upper segment of the integrated reactor conducts a plasma reaction to produce gaseous hydrogen peroxide. Through calibration by conventional iodometry, the yield of hydrogen peroxide is about 0.35 g/h. (2) The two segments of reactors are integrated for the gas phase epoxidation of propylene and hydrogen peroxide. After the calibration step, firstly the discharge is stopped, then the oxygen is stopped, and the hydrogen is stopped after 10 minutes. 0.5 g of modified large-crystal micron-sized TS-1 zeolite (tableted, crushed, and sieved to obtain 20-40 meshes in advance according to conventional methods) is loaded into the lower segment of fixed bed epoxidation reactor, and the lower segment of reactor and the upper segment of reactor are connected together. The lower segment of reactor is inserted into an electric heating furnace. Next, the self-cooling circulating water of the upper segment of reactor is opened. Then, a hydrogen cylinder and the mass flow controller are started to control the hydrogen flow to be 170 ml/min; and next, the oxygen cylinder and the mass flow controller are started to slowly increase the oxygen flow to be 8 ml/min. The flows of the hydrogen and the oxygen are accurately controlled and the hydrogen and the oxygen shall be mixed uniformly before entering the upper segment of reactor. Then, propylene feed of the lower segment of reactor is started, and propylene flow is controlled to be 18 ml/min by the mass flow controller. After the three gas flows are stable and the cooling water flow of the upper segment of reactor is also stable, a plasma power supply of the upper segment of reactor is turned on for dielectric barrier discharge. In this way, hydrogen peroxide gas synthesized by the discharge of the upper segment is carried by excess hydrogen to enter the epoxidation reactor in the lower segment from a gas hole between the two segments of reactors, and is fully mixed with propylene gas which enters the segment of reactor from a side line to jointly enter the TS-1 catalyst bed for conducting the epoxidation. The actual molar ratio of propylene and hydrogen peroxide is calculated to be about 5:1. The reaction temperature of the lower segment of reactor is controlled as 130° C. through the electric heating furnace. After the discharge is conducted for 30 minutes, through online gas chromatography (analysis by DB-Wax chromatographic column (30 m×0.32 mm, PEG20M) (temperature programming to 50° C. for 5 minutes, at 10° C. to 180° C. per minute for 2 minutes, at 20° C. to 200° C. per minute for 5 minutes), the reaction product is analyzed, from the analysis data propylene conversion rate is calculated, which is 15.5%; the PO selectivity is calculated, which is 97.0%; and the utilization rate of hydrogen peroxide is calculated, which is 77.5%.

Reference embodiment 1. The reference embodiment 1 is used to illustrate that the unmodified large-crystal micron-sized TS-1 zeolite has poor activity and selectivity for the gas phase epoxidation of propylene and hydrogen peroxide, and the utilization rate of hydrogen peroxide is low.

The embodiment 1 is repeated, but the large-crystal micron-sized TS-1 zeolite synthesized in the first step is directly used for the evaluation of propylene gas phase epoxidation in the fixed bed reactor without the subsequent hydrothermal modification using the sodium hydroxide solution. Then, propylene conversion rate is 4.5%, the PO selectivity is 56.2%, and H$_2$O$_2$ utilization rate is 22.5%.

Embodiment 2. The present embodiment is used to illustrate that when an alkali metal ion modified large-crystal micron-sized TS-1 zeolite is prepared on an enlarged scale according to the degree controlled hydrothermal treatment method of the alkali metal hydroxide solution provided by the present invention, a small amount of the modified zeolite is tableted, formed and evaluated on the small fixed bed reactor first to confirm its high activity and selectivity and utilization rate of hydrogen peroxide for the gas phase epoxidation of propylene and hydrogen peroxide. After that, the modified TS-1 zeolite is used for spray forming to prepare the microspherical catalyst (the content of the zeolite is only 50%); and the microspherical catalyst is then used for the gas-solid phase fluidized propylene epoxidation. The results are surprising: in the gas-solid phase fluidized reaction mode, the epoxidation results of the microspherical TS-1 catalyst with a zeolite content of only 50% are actually equivalent to the epoxidation results of the tableted modified TS-1 zeolite (zeolite content of 100%) in the fixed bed reaction mode. The implementation process is as follows:

At first step: synthesizing and preparing the large-crystal micron-sized TS-1 zeolite matrix on scale-up according to the method introduced in Appl. Catal. A, 185, (1999) 11-18.

The specific feed amount and synthesis steps are as follows:

11 l of deionized water is added to 11.25 kg of silica sol (26% wt); after stirring for 10 minutes, 920 g of tetrapropylammonium bromide is added to a diluted silica sol solution; after continuing stirring for 20 minutes, a raw silicon solution is obtained; tetrabutyl titanate and acetylacetone are mixed at a mass ratio of 1:0.8, and stirred for 15 minutes to prepare a titanium solution; 985 ml of titanium solution is added to the silicon solution; after stirring for 30 minutes, 2.85 l of n-butylamine is added and continuously stirred for 15 minutes to obtain uniform gel; then the obtained gel is added to a 100 l stainless steel hydrothermal synthesis autoclave and the hydrothermal synthesis is carried out at 170° C. for 96 hours under agitation. After the crystallization time is reached, the hydrothermal crystallization autoclave is naturally cooled to room temperature at first, then the autoclave is opened, and the mother solution is removed by a plate and frame filter to obtain a zeolite filter cake. The filter cake is washed with deionized water for several times until the pH value of the washing solution is close to 7.0. Then, the filter cake is put into an electric oven and dried overnight at 110° C. The dried solid is then transferred into a muffle furnace for temperature-programmed calcination to remove the templating agent. The temperature-programmed calcination starts at room temperature, and the temperature is raised to 300° C. at a temperature rise rate of 10° C./min, and then the temperature is raised from 300° C. to 500° C. at a temperature rise rate of 1° C./min and kept constant until the sample is completely white, so as to obtain about 2.7 kg of large-crystal micron-sized TS-1 zeolite matrix.

In order to use a reference samples to calculate the relative crystallinity of the large-crystal micron-sized TS-1 matrix, embodiment 1 in the Chinese invention patent (application number) 201110295555.x is used to prepare the reference samples. Specifically: 220 ml of deionized water is added to 225 g of silica sol (20% wt); after stirring for 10 minutes, 18.4 g of tetrapropylammonium bromide and 5.1 g of seed crystals are added to the diluted silica sol solution; after continuing stirring for 20 minutes, a silicon solution is obtained; tetrabutyl titanate and acetylacetone are mixed at a mass ratio of 1:0.8, and stirred for 15 minutes to prepare a titanium solution; 19.7 ml of the titanium solution is added to the silicon solution; after stirring for 30 minutes, 57 ml of n-butylamine is added and continuously stirred for 15 minutes to obtain uniform gel; then 6.0 g of $Na_2SO_4$ is added and stirred for 10 minutes; and then the obtained gel is added to a 2 l stainless steel autoclave and crystallized at 170° C. for 24 hours under agitation. The post-treatment method of the reference sample is conducted by referring to the processing method of the large-crystal micron-sized TS-1 zeolite matrix.

SEM, XRF, FT-IR and XRD are used to characterize the large-crystal micron-sized TS-1 zeolite matrix. Results show that the crystal size is 1×2×6 μm, the total Si/Ti molar ratio is about 39.0, and the sodium-titanium molar ratio is 0.002. The index value $I_{960\ cm-1}/I_{550\ cm-1}$ of the framework titanium content is about 0.50 and the relative crystallinity is about 100%. The measurement results show that the synthesized large-crystal micron-sized TS-1 matrix meets the requirements of the present invention.

At second step: preparing 0.1 mol/L sodium hydroxide modification solution.

The solution is prepared with analytically pure sodium hydroxide solid particles (96%) and deionized water. Firstly, 50 l of deionized water is added to a solution preparing tank, and then 208.5 g of sodium hydroxide solid particles are accurately added to the solution preparing tank under stirring. After the sodium hydroxide solid particles are completely dissolved, 0.1 mol/L sodium hydroxide solution (cooled to room temperature) is prepared. For the sake of caution, a standard reagent potassium hydrogen phthalate and a phenolphthalein indicator are used to calibrate the prepared sodium hydroxide solution in accordance with conventional operation. A qualified solution has a relative deviation of the concentration value of less than 5%. Otherwise, the modification solution is prepared again.

At third step: using 0.1 mol/L sodium hydroxide solution to the conduct the degree controlled hydrothermal treatment on the large-crystal micron-sized TS-1 zeolite matrix.

Specifically, the degree controlled hydrothermal modification is conducted in a hydrothermal synthesis autoclave with heat transfer fluid heating. Firstly, 22 l of calibrated 0.1 mol/L sodium hydroxide solution is added to the hydrothermal autoclave. Then, 2.2 kg of the large-crystal micron-sized TS-1 matrix that is calcined in the first step and completely removed from the templating agent is added under stirring. After stirring for 2 hours at room temperature, hot heat transfer fluid is used to heat the synthesis autoclave to increase the temperature. The hydrothermal autoclave is heated to 170° C. in about 4 hours. Then, the temperature is constant for 18 hours under stirring; and in this period, the temperature is controlled at 170±1° C. After the hydrothermal treatment is finished, the hot heat transfer fluid is replaced with cold heat transfer fluid to quickly cool the hydrothermal autoclave to room temperature.

At fourth step: conducting post-treatment on the modified TS-1 zeolite.

The modification solution is removed by the plate and frame filter to obtain a modified zeolite filter cake. The filter cake is washed with 0.01 mol/L sodium hydroxide solution until no precipitate appears after the filtrate is neutralized with acid. Then, the filter cake is put into the electric oven and dried overnight at 110° C. to ensure that the dry basis content of the solid powder (solid content measured after calcining at 500° C. for 3 hours) is not less than 90%. Finally, the dried solid powder is calcined at a constant temperature of 540° C. for 6 hours to obtain the modified product.

The modified TS-1 zeolite prepared in the present embodiment is tested and evaluated below: Firstly, infrared spectroscopy is used to characterize the absorption peak position of the framework titanium of the sodium ion modified TS-1 zeolite.

An appropriate amount of the modified product in the fourth step is put into a small beaker; an appropriate amount of spectral purity KBr is put into another small beaker; and the two small beakers are simultaneously put into the oven at 110° C. for pre-drying for 4 hours. Then KBr and the modified TS-1 product are mixed and ground at a ratio of 200:1, and pressed into a wafer under a pressure of 6 MPa; the wafer is put into an infrared sample cell for testing to obtain an infrared spectrum; and finally, the second derivative spectrum in the infrared software is used to accurately locate the infrared characteristic absorption peak position of the framework titanium active site modified by the alkali metal ions, which is at 969 $cm^{-1}$ for the modified zeolite product of embodiment 2.

In addition, the X-ray fluorescence spectroscopy (XRF) method mentioned in the first step is used to obtain the silicon-titanium molar ratio and sodium-titanium molar ratio of the modified zeolite product of embodiment 2, which are 37.5 of 0.87, respectively.

The characterization results of the infrared spectroscopy and the X-ray fluorescence spectroscopy show that the hydrothermal treatment of the large-crystal micron-sized TS-1 zeolite matrix with 0.1 mol/L sodium hydroxide solution produces a controllable silicon dissolution effect, so that the silicon-titanium molar ratio of the modified zeolite is slightly lower than that of the matrix. At the same time, a large amount of sodium ions exist in the modified zeolite, which makes that the infrared characteristic absorption peak of the framework titanium active site shift from 960 cm$^{-1}$ to 969 cm$^{-1}$. Namely, in the process of degree controlled hydrothermal treatment modification for the large-crystal micron-sized TS-1 zeolite matrix with 0.1 mon sodium hydroxide solution, the sodium ions replace the hydrogen protons on the silicon hydroxyl near the framework titanium in the form of counter cations, and therefore change the local environment of the nearby framework titanium site.

Then, a small fixed bed reactor is used to evaluate the gas phase epoxidation performance of the sodium ion modified TS-1 zeolite. Embodiment 1 provides the detailed description. Based on the evaluation, the conversion rate of propylene is 15.2%, the PO selectivity is 97.4% and the utilization rate of hydrogen peroxide is 76.0%.

At fifth step: processing the sodium ion modified TS-1 into a microspherical catalyst by a spray forming method.

The engineers familiar with the field can complete the work of the step according to own experience or following the practice of the literature. The reference practice provided by the present invention is as follows:

(1) The suspension of the modified TS-1 zeolite is prepared with the acidic hydrolysis solution of tetraethyl orthosilicate. About 6 kg of tetraethyl orthosilicate is added to 5.5 kg of deionized water under stirring. Then, 63.5% concentrated nitric acid is dropwise added to the solution to hydrolyze estersil at room temperature under the acidic condition of solution pH=3.0 to obtain a binder glue solution. 1.8 kg of sodium ion modified TS-1 zeolite is dispersed in the binder glue solution which is not dealcoholized, and the dispersion liquid is treated with a colloid mill to make the particle size $D_{90}$ of particulate matter less than or equal to 8 microns, thereby obtaining a zeolite suspension for spray forming. The total solid content (TS-1 zeolite and silicon oxide) in the zeolite suspension is calculated as about 27 wt %; and the ratio of the zeolite to the solid content is about 50 wt %.

(2) The spray forming is conducted in a rotating spray drying tower made in China The diameter of the drying tower is 2.5 m; the feeding rate is 20 kg/h; and the working rotating speed of a rotating atomizer is 8000 min'. The temperature of hot air entering the tower is 350° C., and the temperature of exhaust air exiting the tower is 120° C.

(3) 4.2 kg of crude spray forming product (wet basis) are collected from the rotating spray drying tower. The crude products are dried overnight at 110° C.; when confirming that the dry basis content is not less than 90 wt %, drying is stopped; and the dried products are collected. Then, an appropriate amount of the dried products is calcined at 600° C. for 6 hours to obtain a microspherical sodium ion modified TS-1 catalyst sample.

Figure 2:
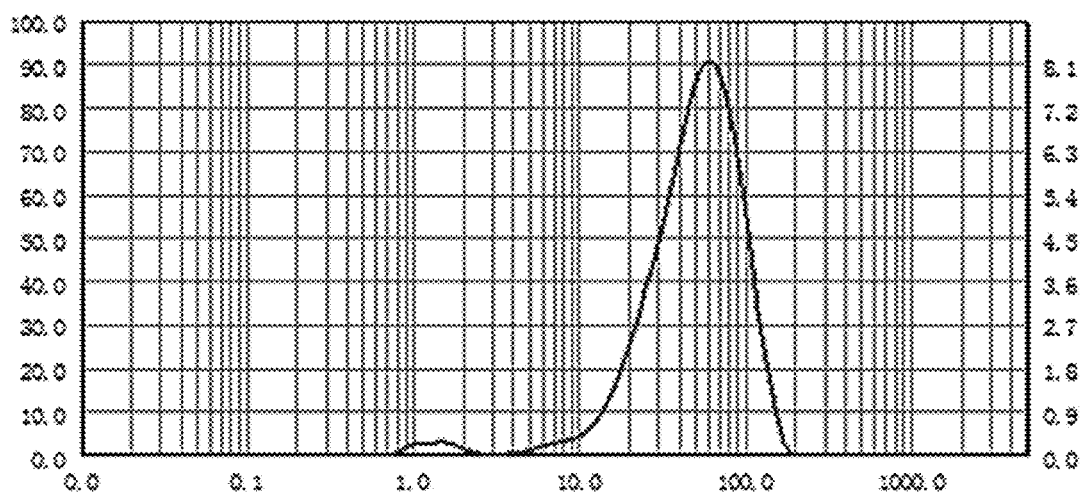
FIG. 2 is the crystal size distribution diagram of a spray forming sodium ion modified TS-1 catalyst in embodiment 2 obtained by a laser particle analyzer.

(4) The particle size distribution of the microspherical sodium ion modified TS-1 catalyst sample measured by the Bettersize 2000 laser particle size distribution meter made in China is shown in FIG. 2. The volume average particle size is about 57 microns, and D50 and $D_{90}$ values are respectively 52 microns and 101 microns.

Figure 3:
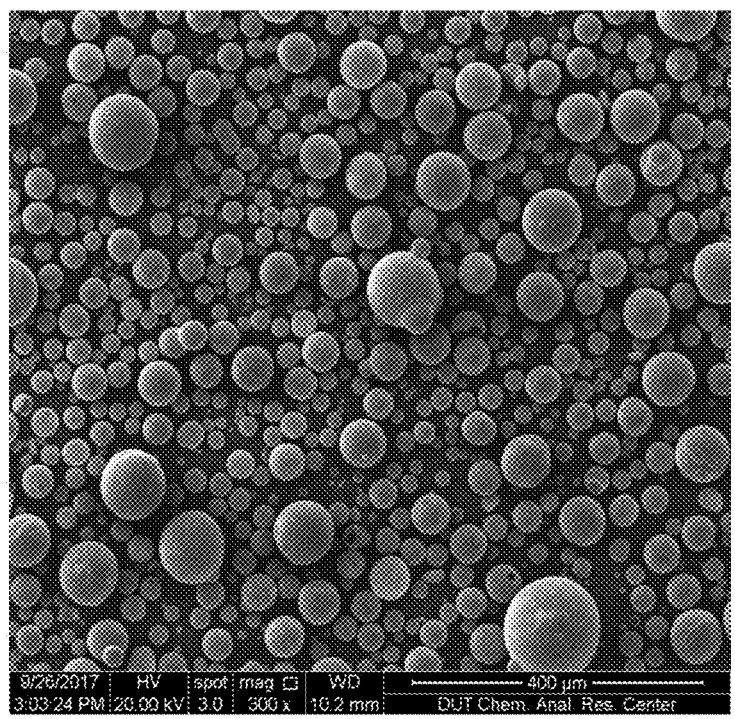
FIG. 3 is the scanning electron microscope (SEM) image of a spray forming sodium ion modified TS-1 catalyst in embodiment 2.

(5) The scanning electron microscope image of the microspherical sodium ion modified TS-1 catalyst sample obtained by a scanning electron microscope (SEM) is shown in FIG. 3.

At sixth step: conducting the gas phase epoxidation of propylene and hydrogen peroxide in a gas-solid phase fluidized state by using a bubbling bed fluidized reactor.

The sizes of the used reactor are: the reaction zone (dense phase region) has a tube inner diameter of 6 mm and a length of 25 mm, and the recirculation zone (dilute phase region) has a tube inner diameter of 20 mm and a length of 30 mm. In order to facilitate the observation of the fluidized state of the catalyst, the shell of the reactor is made of quartz glass. Firstly, 0.5 g of microspherical alkali metal ion modified TS-1 catalyst is loaded into the reactor, and then the reactor is installed on the reaction device. The feed amount of propylene feed gas is controlled as 45 ml/min by a mass flowmeter; the feed amount of hydrogen peroxide solution (an aqueous solution having hydrogen peroxide content of 50%, industrial premium grade) is controlled as 2.2 g/h by a peristaltic pump; and the molar ratio of propylene to hydrogen peroxide is 4:1. Hydrogen peroxide solution comes into contact with propylene feed gas before entering the reactor, and is fully vaporized in the contact process. Thus, propylene feed gas shall be preheated by a propylene feed preheater before coming into contact with hydrogen peroxide solution. Based on experience, the heating temperature of the preheater is set as 150° C. In order to adjust the fluidized state of the catalyst, nitrogen is used as the diluent gas of propylene in the experiment. The nitrogen flow is controlled as 165 ml/min by the mass flowmeter. The nitrogen and propylene feed gas are mixed before the preheater. When hydrogen peroxide solution comes into contact with the preheated mixture of propylene and the nitrogen, hydrogen peroxide solution is instantly vaporized, then enters the bottom of the reactor together with the mixture of propylene and the nitrogen, and then penetrates through a quartz sieve plate distributor to come into contact with the microspherical alkali metal ion modified TS-1 catalyst to carry out a gas-solid phase fluidized propylene epoxidation (the gas overall line speed is 0.12 m/s, and the fluidized state belongs to a low-speed bubbling bed). The bottom space of the reactor and the quartz sieve plate distributor provide sufficient mixing conditions for propylene and hydrogen peroxide gas. During the gas-solid phase fluidized epoxidation of propylene and hydrogen peroxide gas, the molar ratio of propylene and hydrogen peroxide is kept as 4:1; the heater temperature of the reactor is 130° C.; and reaction products and the conversion rate of propylene are quantitatively analyzed by online gas chromatography. A hydrogen flame detector and DB-Wax chromatographic columns (30 m×0.32 mm, PEG20M) are adopted by the online gas chromatography to operate as follows: temperature programming to 50° C. for 5 minutes, at 10° C. to 180° C. per minute for 2 minutes, at 20° C. to 200° C. per minute for 5 minutes. The reaction results are: the conversion rate of propylene is 18.7%, the PO selectivity is 97.3% and the utilization rate of hydrogen peroxide is about 75.0%.

Reference embodiment 2. The reference embodiment 2 is used to illustrate that if the microspherical alkali metal ion modified TS-1 catalyst prepared in the fifth step of embodiment 2 is tableted and used for the gas phase epoxidation of propylene and hydrogen peroxide in the fixed bed reaction mode, the decomposition rate of hydrogen peroxide is increased and the utilization rate is reduced.

The embodiment 2 is repeated. However, the microspherical TS-1 catalyst prepared in the fifth step is tableted, crushed, and sieved to form a fixed bed catalyst (having particle size of 20-40 meshes); then a catalyst sample of 20-40 meshes is loaded into a small bubbling bed reactor; an appropriate amount of quartz sand is added on the catalyst to compact the catalyst bed; the microspherical catalyst is not fluidized in propylene-nitrogen feed gas containing hydrogen peroxide; propylene epoxidation is forced to occur in the fixed bed reaction mode; and the feed amount and reaction conditions are the same as those in the sixth step of embodiment 1. The obtained conversion rate of propylene is 16.3%, the PO selectivity is 97.1% and the utilization rate of hydrogen peroxide is 65.3%.

It is easily found from comparison of the reference embodiment 2 and embodiment 2 that under the same reaction conditions, the gas-solid phase fluidized reaction mode is more conducive to inhibiting the decomposition of hydrogen peroxide and increasing the utilization rate of hydrogen peroxide than the fixed bed reaction mode.

Embodiment 3. The present embodiment is used to illustrate that if the ratio of the modified zeolite to the solid content is appropriately reduced in the fifth step of preparing the microspherical alkali metal ion modified TS-1 catalyst in embodiment 2, the microspherical catalyst still has good catalytic performance for propylene epoxidation in the gas-solid phase fluidized mode.

The embodiment 2 is repeated. However, in the fifth step, when the microspherical TS-1 catalyst is prepared by the spray forming method, if the amount of the modified TS-1 zeolite added to the binder glue solution is reduced to 1.15 kg and 0.74 kg, respectively, then the ratios of the zeolite to the solid content are 40 wt. % and 30 wt. %, respectively. The results of the gas-solid phase fluidized epoxidation of the prepared microspherical sodium ion modified TS-1 catalyst in the sixth step are successively as follows: the conversion rates of propylene are 15.8% and 12.5%, the PO selectivities are 97.1% and 97.4%, and the utilization rates of hydrogen peroxide are 63.3% and 49.8%.

Embodiment 4. The present embodiment is used to illustrate that if the ratio of the modified zeolite to the solid content is increased in the fifth step of preparing the microspherical alkali metal ion modified TS-1 catalyst in embodiment 2, the conversion rate of propylene and the utilization rate of hydrogen peroxide of propylene epoxidation of the microspherical catalyst in the gas-solid phase fluidized mode cannot be significantly improved.

The embodiment 2 is repeated. However, in the fifth step, when the microspherical TS-1 catalyst is prepared by the spray forming method, if the addition amount of the modified TS-1 zeolite in the binder glue solution is increased to 2.60 kg and 4.04 kg, respectively, then the ratios of the zeolite to the solid content are 60 wt. % and 70 wt. %, respectively. The results of the gas-solid phase fluidized epoxidation of the prepared microspherical sodium ion modified TS-1 catalyst in the sixth step are successively as follows: the conversion rates of propylene are 17.7% and 18.2%, the PO selectivities are 97.0% and 97.2%, and the utilization rates of hydrogen peroxide are 70.7% and 72.8%.

Embodiment 5. The present embodiment is used to illustrate that if the binder glue solution is subjected to alcohol distilling pretreatment in the fifth step of preparing the microspherical alkali metal ion modified TS-1 catalyst in embodiment 2, the total solid content (TS-1 zeolite and silicon oxide) in the zeolite suspension can be adjusted so as to adjust the particle size distribution and average particle size of the microspherical alkali metal ion modified TS-1 catalyst.

The embodiment 2 is repeated, but the binder glue solution is subjected to alcohol distilling pretreatment in the fifth step of preparing the microspherical alkali metal ion modified TS-1 catalyst. The alcohol distilling pretreatment is conducted at temperature of 55-60° C. and negative pressure (e.g., −0.08 MPa). By controlling the alcohol distilling time, the zeolite suspensions having the solid contents (TS-1 zeolite and silicon oxide) of 30 wt % and 35 wt % are obtained and the ratios of the zeolite to the solid contents are 50 wt %. The volume average particle sizes of the microspherical sodium ion modified TS-1 catalyst sample measured by the laser particle size distribution analyzer are 63 microns and 67 microns, respectively; D50 values are 59 microns and 63 microns, respectively; and D90 values are 112 microns and 117 microns, respectively.

Reference embodiment 3. The reference embodiment 3 is used to illustrate that if the large-crystal micron-sized TS-1 zeolite matrix is treated according to the sodium exchange method provided in J. Catal., 1995, 151, 77-86, the obtained modified zeolite has no improvement effect on the gas phase epoxidation of propylene and hydrogen peroxide.

The embodiment 1 is repeated, but the large-crystal micron-sized TS-1 zeolite synthesized in the first step is not modified by the hydrothermal modification method of the sodium hydroxide solution provided by the present invention, but is modified in accordance with the sodium exchange method provided by J. Catal., 1995, 151, 77-86. The specific method is as follows: 1 mol/L NaOH solution is prepared, and then 1 g of zeolite matrix is added to 100 mL of 1 mol/L NaOH solution, and stirred at 25° C. for 24 hours. Then the solution is subjected to suction filtration, dried at 110° C. for 12 hours, and calcined at 540° C. for 6 hours.

Then, the silicon-titanium molar ratio of the sodium exchange TS-1 zeolite measured by XFR is reduced to 30, and the sodium-titanium molar ratio is 1.40. The infrared characteristic absorption peak of the framework titanium measured by the infrared spectroscopy appears at 985 cm$^{-1}$ (FIG. 1C), which is consistent with the literature report. By comparing with the analysis results of the matrix, it can be found that the silicon-titanium molar ratio of the TS-1 zeolite product modified by the sodium exchange method is reduced significantly, indicating that the modification of the sodium exchange method reported in the literature for the TS-1 matrix is not a degree controlled modification. Instead, it is a method of excessive dissolution of silicon. Although the sodium exchange zeolite contains a large amount of sodium ions which are combined with the silicon hydroxyl in the form of counter cations, which causes the shift of the characteristic absorption peak position of the framework titanium from 960 cm$^{-1}$ (matrix) to the high wave number direction, the peak at 985 cm$^{-1}$ is 16 wave numbers higher than the sodium ion modified TS-1 zeolite of embodiment 1. It can be concluded that a substantial difference exists between the sodium ion modified TS-1 zeolite obtained by the method of the present invention in embodiment 1 and the modified zeolite obtained by the sodium exchange method in the reference embodiment 3.

The evaluation results of propylene gas phase epoxidation provided by the fixed bed reactor show that the modified zeolite prepared by the sodium exchange method reported in the literature in the reference embodiment 3 has a propylene conversion rate of only 2.3%, a PO selectivity of 81.3%, and a $H_2O_2$ utilization rate of only 10.5%. In other words, the performance of the modified zeolite obtained by the sodium exchange method in the gas phase epoxidation of propylene and hydrogen peroxide is not better than that of the matrix. In fact, the modified zeolite can be considered as basically having no epoxidation activity. However, the modified zeolite has high activity for the self-decomposition reaction of hydrogen peroxide, so that the utilization rate of hydrogen peroxide is only 8.7%.

Reference embodiment 4. The reference embodiment 4 is used to illustrate from the opposite side that when the large-crystal micron-sized TS-1 zeolite matrix is modified according to the degree controlled hydrothermal treatment method of the alkali metal hydroxide solution provided by the present invention, it is important that sodium ions are retained in the modified zeolite.

The embodiment 1 is repeated, but after the operation of the fourth step is completed, the modified titanium silicalite zeolite is subjected to conventional ammonium exchange treatment twice with 0.4 M ammonium nitrate at room temperature, each for 2 hours. The engineers familiar with the field can complete the ammonium exchange work described in the reference embodiment 2 according to the method for preparing hydrogen catalysts through ammonium exchange of silica-alumina zeolite reported by any publication literature. After the ammonium exchange, the solution is removed by Buchner funnel suction filtration to obtain a zeolite filter cake. Then, the filter cake is put into the electric oven and dried overnight at 110° C. to ensure that the dry basis content of the solid powder (solid content measured after calcining at 500° C. for 3 hours) is not less than 90%. Finally, the dried solid powder is calcined at a constant temperature of 540° C. for 6 hours to obtain an ammonium exchange zeolite product. Then, the ammonium exchange zeolite product is used for composition analysis and propylene gas phase epoxidation of the fixed bed. Then the sodium-titanium ratios measured by XRF for samples of one-time and two-time ammonium exchange are 0.25 and 0.18 respectively. By using the fixed bed reactor, the conversion rates of propylene are respectively 7.6% and 5.7%; PO selectivities are respectively 83.6% and 34.8%; and the utilization rates of hydrogen peroxide are respectively 34.6% and 25.9%.

The reference embodiment 4 illustrates that after the sodium ion modified TS-1 zeolite obtained in the embodiment 1 is subjected to conventional ammonium exchange to remove the balanced sodium ions on the silicon hydroxyl to different degrees, the conversion rate of the gas phase epoxidation and the utilization rate of hydrogen peroxide are significantly decreased. The more the sodium ion content decreases, the more the gas phase epoxidation performance of the modified zeolite decreases. This fully demonstrates that the presence of sufficient sodium ions in the modified TS-1 zeolite is the key to present a good modification effect in the modified zeolite of the present invention. It can also be seen from the comparison of the selectivity of propylene oxide that the degree controlled inorganic base hydrothermal treatment method provided by the present invention may produce some acidic sites in the catalyst due to the effect of silicon dissolution. The presence of the sodium ions neutralizes these acid sites at the same time, so that the modified zeolite of embodiment 1 reaches high selectivity close to 98%. However, in the reference embodiment, because most sodium ions are removed through the ammonium exchange, these acid sites produced by the modification are exposed, thereby causing very low selectivity of the ammonium exchange zeolite, which is even lower than the selectivity (<35%) of propylene oxide of the matrix.

Reference embodiment 5. The reference embodiment 5 is used to further illustrate that when the large-crystal micron-sized TS-1 is modified according to the degree controlled hydrothermal treatment method provided by the present invention, it is important that enough sodium ions are retained in the modified zeolite.

The reference embodiment 4 is repeated, but after the ammonium exchange catalyst is obtained, the ammonium exchange catalyst is subjected to reverse exchange treatment of the sodium nitrate solution at room temperature for 2 hours. The reverse exchange of the sodium nitrate solution is a conventional ion exchange treatment, and the practice is roughly the same as the ammonium exchange in the reference embodiment 4, except that the ammonium salt solution is changed to the sodium nitrate solution. The engineers familiar with the field can complete the work according to the zeolite ion exchange method recorded in any publication literature. After the ion exchange of the sodium nitrate solution is completed, the separation, drying and calcining operations after the ammonium exchange are repeated. The obtained sodium nitrate exchange zeolite is used for composition analysis and propylene gas phase epoxidation of the fixed bed.

When the concentrations of the sodium nitrate solution are respectively 0.1 M and 0.3 M, the sodium-titanium ratios of the sodium nitrate exchanged zeolite product measured by XRF are 0.39 and 0.72; the conversion rates of propylene obtained by the fixed bed reactor are 7.6% and 13.3% in sequence; the PO selectivities are 78.6% and 95.2% in sequence; and the utilization rates of hydrogen peroxide are 34.6% and 60.5% in sequence.

The above results can further indicate that when the large-crystal micron-sized TS-1 zeolite matrix is modified according to the degree controlled hydrothermal treatment method of the alkali metal hydroxide solution provided by the present invention, it is important that sodium ions are retained in the modified zeolite. Meanwhile, the reference embodiment 5 can also illustrate that for the ammonium exchange modified zeolite, the lost sodium ions can be supplemented with sodium through sodium salt reverse exchange, thereby recovering the catalytic performance of the gas phase epoxidation of the modified zeolite.

Figure 4:
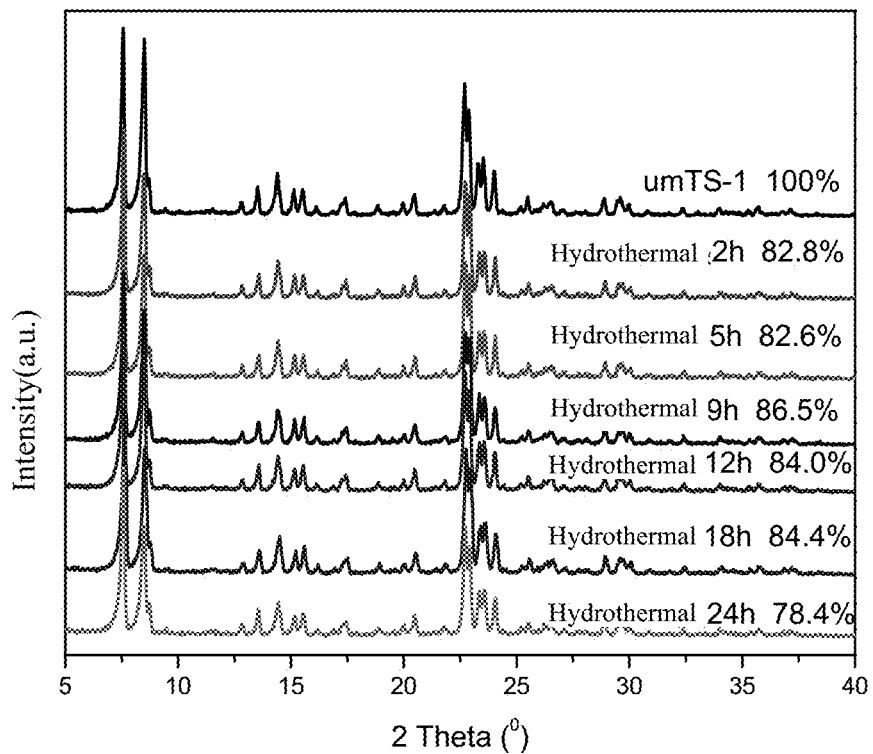
FIG. 4 shows the XRD patterns of a catalyst sample of embodiment 6.
Figure 5:
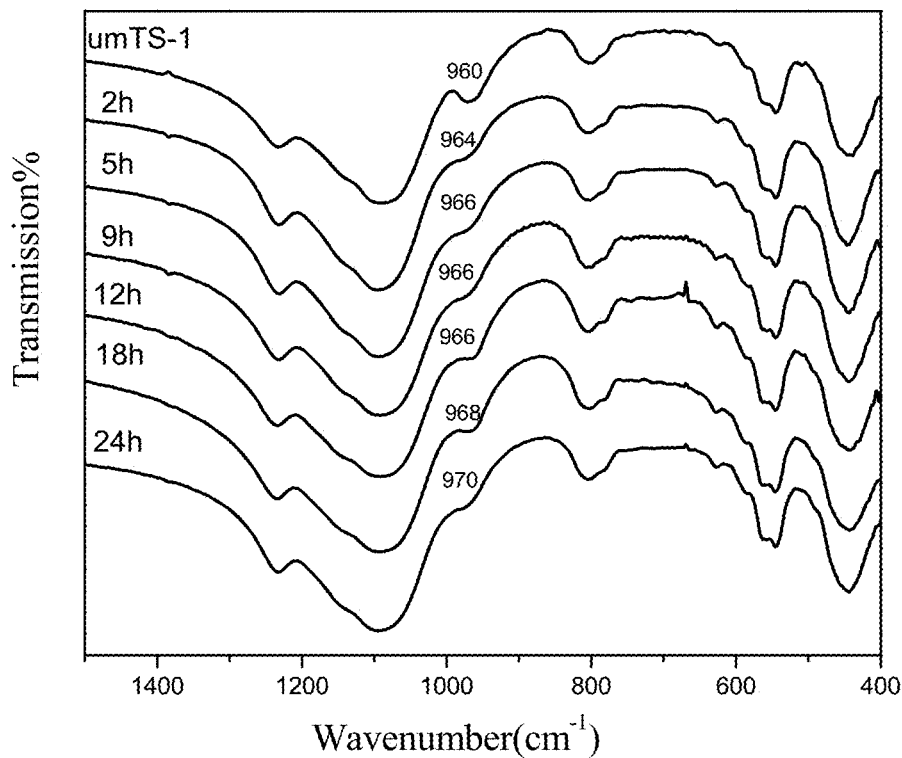
FIG. 5 shows the framework vibration FT-IR spectra of a catalyst sample of embodiment 6.

Embodiment 6. The present embodiment is used to illustrate that by changing a modification time parameter, the degree of hydrothermal modification of the TS-1 zeolite by the alkali metal hydroxide solution can be adjusted, and the performance of the gas phase epoxidation of propylene and hydrogen peroxide is changed accordingly The embodiment 1 is repeated, but in the operation of the third step, the duration of hydrothermal treatment modification is changed to 2, 5, 9, 12 and 24 hours, respectively. Then, the relative crystallinity data (FIG. 4) of the samples are 82.8%, 82.6%, 86.5%, 84.0% and 78.4% in sequence; the silicon-titanium molar ratio data are 37.9, 37.8, 37.9, 37.6 and 37.6 in sequence; the sodium-titanium molar ratio data are 0.91, 0.87, 0.87, 0.85 and 0.75 in sequence; and the positions of the infrared characteristic absorption peaks (FIG. 5) of the framework titanium active sites are at 964, 966, 966, 966 and 970 cm' in sequence. The results of the gas phase epoxidation of propylene and hydrogen peroxide evaluated in the fixed bed reactor are as follows: the conversion rates of propylene are 5.6%, 6.5%, 8.9%, 10.2% and 12.0% in sequence; the PO selectivities are 88.5%, 88.6%, 94.3%, 94.6% and 96.9% in sequence; and the utilization rates of hydrogen peroxide are 28.0%, 32.5%, 44.5%, 51.0% and 60.0% in sequence. As mentioned above, the hydrothermal treatment time adopted in embodiment 1 is 18 hours, and the conversion rate of propylene, the PO selectivity, and the utilization rate of hydrogen peroxide of the obtained sodium ion modified TS-1 zeolites are 15.5%, 97.0% and 77.5% respectively.

It can be seen that the hydrothermal treatment time has a suitable region. Therefore, the present invention provides a preferred range of 10-20 hours, and a more preferred range of 15-20 hours.

However, from the comparison with the reaction result of the matrix (reference embodiment 1), it can be seen that the modification effectiveness of the modification method provided by the present invention for the modification of the TS-1 matrix can be reflected in a wide time range.

Figure 6:
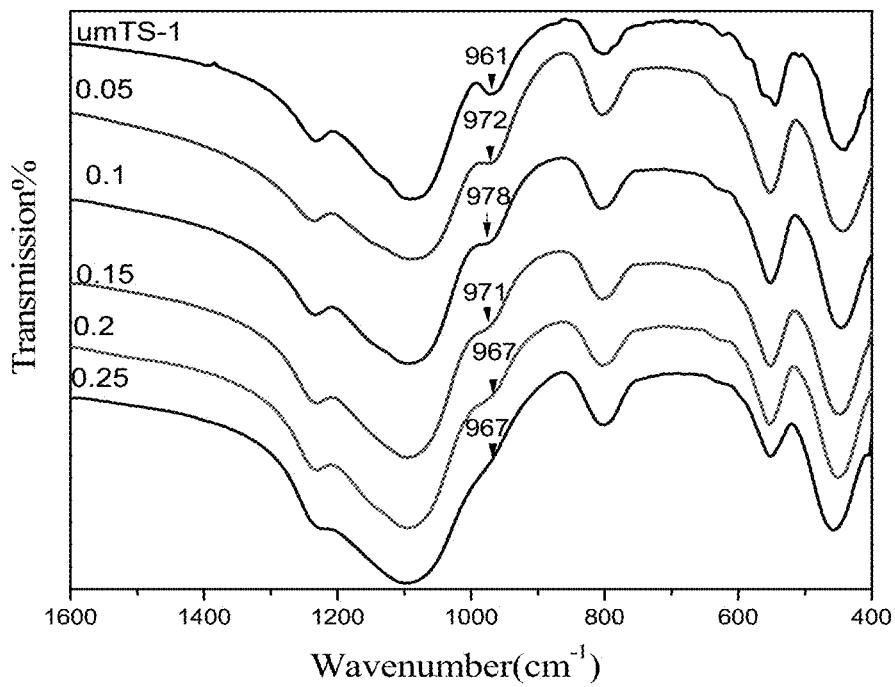
FIG. 6 shows the framework vibration FT-IR spectra of a catalyst sample of embodiment 7.

Embodiment 7. The present embodiment is used to illustrate that by changing a concentration parameter of the alkali metal hydroxide solution, the degree of hydrothermal modification of the TS-1 zeolite can also be adjusted, and the performance of the gas phase epoxidation of propylene and hydrogen peroxide is changed accordingly The embodiment 1 is repeated, but in the operation of the second step, the concentrations of the prepared sodium hydroxide solutions are changed to 0.05, 0.15, 0.20 and 0.25 mon, respectively. Then, the infrared characteristic absorption peak positions of the framework titanium active site of the sodium ion modified TS-1 zeolites measured by the infrared spectroscopy method (FIG. 6) are at 972, 971, 967 and 965 $cm^{-1}$ in sequence; the results of the gas phase epoxidation of propylene and hydrogen peroxide for the above sodium ion modified TS-1 zeolites in the fixed bed reactor are as follows: the conversion rates of propylene are 10.8%, 13.2%, 7.5% and 6.8% in sequence; the PO selectivities are 95.1%, 96.5%, 97.0% and 96.9% in sequence; and the utilization rates of hydrogen peroxide are 54.0%, 66.0%, 37.5% and 34.0% in sequence. Considering that the concentration of the alkali metal hydroxide solution adopted in embodiment 1 is 0.1 mol/L, the conversion rate of propylene, the PO selectivity, and the utilization rate of hydrogen peroxide of the obtained sodium ion modified TS-1 zeolites are 15.5%, 97.0% and 77.5% respectively. It can be seen that the concentration of the alkali metal hydroxide solution also has a suitable region. Therefore, the present invention provides a preferred range of 0.05-0.2 mol/L, and a more preferred range of 0.08-0.15 mol/L.

Similarly, the present invention is intended to state that from the comparison with the reaction result of the matrix (reference embodiment 1), it can be seen that the modification effectiveness of the modification method provided by the present invention for the modification of the TS-1 matrix can be reflected in a wide concentration range of the alkali metal hydroxide solution.

Embodiment 8. The present embodiment is used to illustrate that by changing a temperature parameter, the degree of hydrothermal modification of the TS-1 zeolite by the alkali metal hydroxide solution can be adjusted, and the performance of the gas phase epoxidation of propylene and hydrogen peroxide is changed accordingly The embodiment 1 is repeated, but in the operation of the third step, the temperatures of hydrothermal treatment modification are changed to 25° C., 80° C., 110° C., 150° C., 190° C. and 210° C., respectively. Then, the results of the gas phase epoxidation of propylene and hydrogen peroxide over the obtained sodium ion modified zeolite samples are as follows: the conversion rates of propylene are 4.2%, 6.3%, 9.4%, 13.7%, 12.5% and 7.8% in sequence; the PO selectivities are 90.1%, 92.6%, 97.2%, 97.0%, 96.6% and 97.0% in sequence; and the utilization rates of hydrogen peroxide are 21.0%, 31.5%, 47.0%, 68.5%, 62.5% and 39.0% in sequence. Considering that the hydrothermal treatment temperature adopted in embodiment 1 is 170° C., the conversion rate of propylene, the PO selectivity, and the utilization rate of hydrogen peroxide of the obtained sodium ion modified TS-1 zeolites are 15.5%, 97.0% and 77.5% respectively. It can be seen that the hydrothermal treatment temperature also has a suitable region. Therefore, the present invention provides a preferred range of 100-200° C., and a more preferred range of 150-190° C.

Herein, the present invention is intended to state that from the comparison with the reaction result of the matrix (reference embodiment 1), it can be seen that the modification effectiveness of the modification method provided by the present invention for the modification of the TS-1 matrix can be reflected in a wide range of the hydrothermal treatment temperature.

Embodiment 9. The present embodiment is used to illustrate that by adjusting a liquid-solid ratio parameter, the degree of hydrothermal modification of the TS-1 zeolite by the alkali metal hydroxide solution can be adjusted, and the performance of the gas phase epoxidation of propylene and hydrogen peroxide is changed accordingly The embodiment 1 is repeated, but in the operation of the third step, the liquid-solid ratios of hydrothermal treatment modification are changed to 4, 5, 7 and 15, respectively. The results of the gas phase epoxidation of propylene and hydrogen peroxide in the sodium ion modified TS-1 zeolite samples are as follows: the conversion rates of propylene are 9.7%, 12.6%, 13.5% and 10.8% in sequence; the PO selectivities are 95.2%, 95.7%, 97.3% and 97.5% and in sequence; and the utilization rates of hydrogen peroxide are 48.5%, 63.0%, 67.5% and 54.0% in sequence. Similarly, considering that the liquid-solid ratio adopted in embodiment 1 is 10, the conversion rate of propylene, the PO selectivity, and the utilization rate of hydrogen peroxide of the obtained sodium ion modified TS-1 zeolites are 15.5%, 97.0% and 77.5% respectively. Obviously, the liquid-solid ratio also has a suitable region. Therefore, the present invention provides a preferred range of 5-15, and a more preferred range of 8-12.

Therefore, from the comparison with the reaction result of the matrix (reference embodiment 1), it can be seen that the modification effectiveness of the modification method provided by the present invention for the modification of the TS-1 matrix can be reflected in a wide range of the liquid-solid ratio.

Embodiment 10. The present embodiment is used to illustrate that in the washing step after the hydrothermal treatment, the use of a suitable low-concentration alkali metal hydroxide solution as the washing solution is beneficial to achieve the modification effect.

The embodiment 1 is repeated, but in the post-treatment washing step of the fourth step, deionized water, and 0.001, 0.005 and 0.05 mol/L sodium hydroxide solutions are used to wash the filter cake, respectively. When no precipitation appears after the filtrate is neutralized, the sodium-titanium molar ratio data of the obtained sodium ion modified TS-1 zeolites are 0.48, 0.80, 0.85 and 0.88 in sequence. The results of the gas phase epoxidation of propylene and hydrogen peroxide in the above sodium ion modified TS-1 zeolites are as follows: the conversion rates of propylene are 10.1%, 14.3%, 15.6% and 15.2% in sequence; the PO selectivities are 86.7%, 96.5%, 96.4% and 96.9% in sequence; and the utilization rates of hydrogen peroxide are 50.5%, 71.5%, 78.0% and 76.0% in sequence.

Embodiment 11. The present embodiment is used to illustrate that when the large-crystal micron-sized TS-1 is modified according to the degree controlled hydrothermal treatment method of the alkali metal hydroxide solution provided by the present invention, potassium hydroxide is also effective.

The embodiment 1 is repeated, but in the second step of preparing the hydrothermal modification solution, the potassium hydroxide is used to replace the sodium hydroxide. Then, after the obtained potassium ion modified TS-1 zeolite is analyzed by XRF, the silicon-titanium molar ratio is 37.4 and a potassium-titanium molar ratio is 0.84. The results of the gas phase epoxidation of propylene and hydrogen peroxide presented by the sample in a fixed bed reactor are: the conversion rate of propylene is 15.0%, the PO selectivity is 97.2% and the utilization rate of hydrogen peroxide is 75.0%.

Embodiment 12. The present embodiment is used to illustrate that when the large-crystal micron-sized TS-1 is modified according to the degree controlled hydrothermal treatment method of the alkali metal hydroxide solution provided by the present invention, lithium hydroxide is also effective.

The embodiment 1 is repeated, but in the second step of preparing the hydrothermal modification solution, the lithium hydroxide is used to replace the sodium hydroxide. Then, the results of the gas phase epoxidation of propylene and hydrogen peroxide over the obtained lithium ion modified TS-1 zeolites are: the conversion rate of propylene is 14.5%, the PO selectivity is 96.6% and the utilization rate of hydrogen peroxide is 72.5%.

Embodiment 13. The present embodiment is used to illustrate that the hydrothermal treatment method provided by the present invention can be applicable to a small-crystal micron-sized TS-1 matrix.

Figure 7:
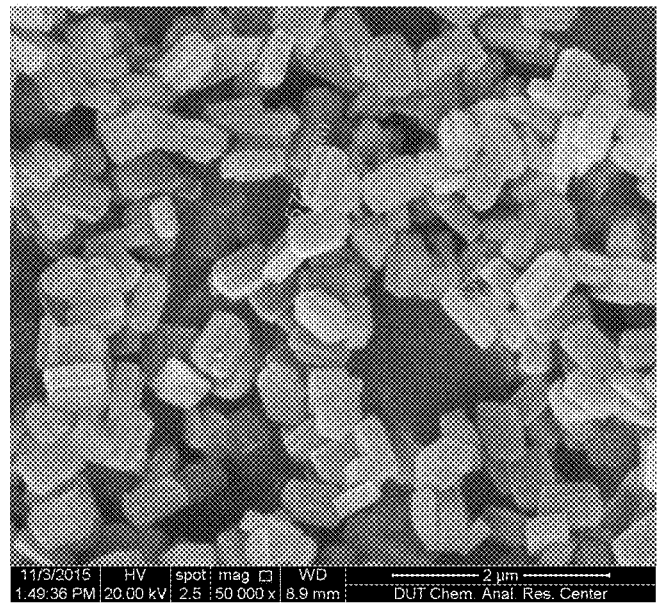
FIG. 7 is the SEM image of small-grained TS-1 matrix adopted in embodiment 13.
Figure 8:
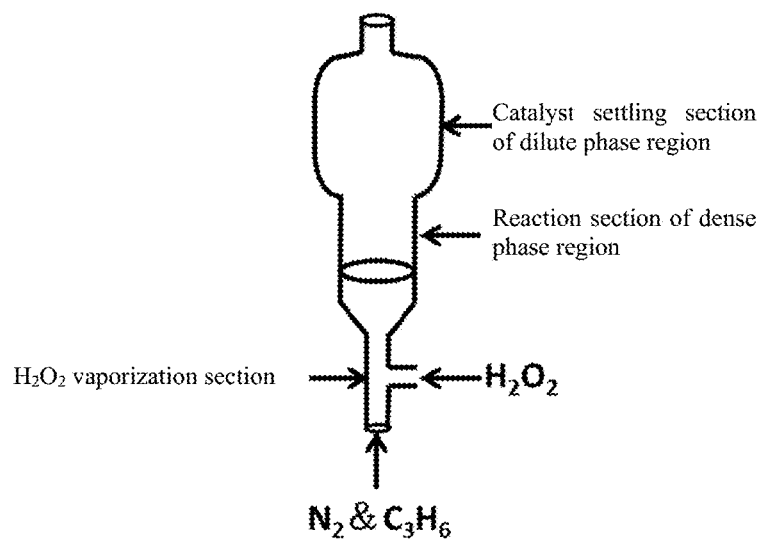
FIG. 8 is the structural diagram of a propylene-hydrogen peroxide gas phase epoxidation bubbling bed fluidized reactor.
Figure 9:
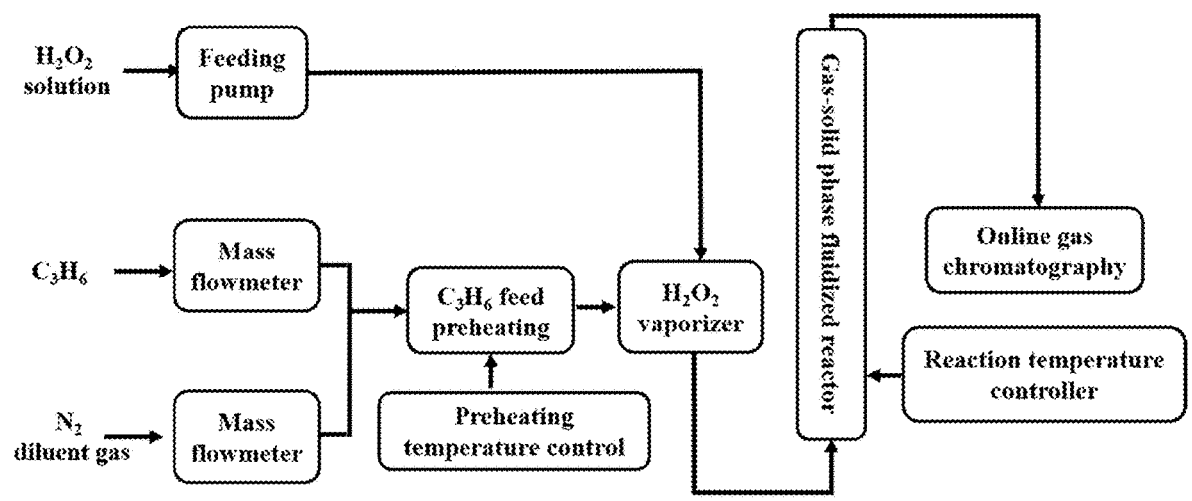
FIG. 9 is the working principle diagram of a propylene-hydrogen peroxide gas phase epoxidation bubbling bed fluidized reactor device.

The embodiment 1 is repeated, but in the first step of hydrothermal synthesis of the TS-1 zeolite matrix, the small-crystal TS-1 matrix that can be used in the present invention is synthesized according to the reference embodiment 1 of the Chinese invention patent (application number) 201310691060.8. The crystal size of the sample provided by the scanning electron microscope (SEM) is about 0.5 micron (FIG. 7). Then, the results of the gas phase epoxidation of propylene and hydrogen peroxide of the obtained sodium ion modified TS-1 zeolites in the fixed bed reactor are: the conversion rate of propylene is 14.7%, the PO selectivity is 96.9% and the utilization rate of hydrogen peroxide is 73.5%.

Reference embodiment 6. The reference embodiment 6 is used to illustrate that the alkali metal ion modified TS-1 zeolite obtained according to the method of the present invention has improvement effects on the gas phase epoxidation of propylene and hydrogen peroxide, but has no obvious improvement effect on the liquid phase epoxidation of propylene and hydrogen peroxide.

The liquid phase epoxidation can be conducted according to the method introduced by any publication literature. Specifically, in the reference embodiment, the liquid phase epoxidation is conducted in a 450 ml stainless steel reactor under water bath temperature control and magnetic stirring. Experimental conditions are as follows: the reaction temperature is 40° C., propylene pressure is 0.6 MPa, and the reaction time is 1 h. The ingredients are as follows: 0.2 g of modified zeolite, 30 ml of methanol and 2 ml of $H_2O_2$ (30%). Before the experiment, the reactor is pressurized with propylene gas, and then gas is vented. The replacement is repeated for 5-6 times in this way for the purpose of replacing the air in the reactor. The concentration of $H_2O_2$ in the product solution is measured by iodometry, and the reaction product is analyzed by chromatography.

TABLE 1

Liquid Phase Epoxidation Data of Propylene and Hydrogen Peroxide of Reference Embodiment 6

| Sample | Liquid Phase Epoxidation (HPPO) Data of Propylene and Hydrogen Peroxide | | |
|---|---|---|---|
| | $X(H_2O_2)$/% | $S(PO)$/% | $U(H_2O_2)$/% |
| umTS-1 | 36.1 | 90.7 | 87.3 |
| Hydrothermal 2 h | 18.1 | 99.2 | 48.0 |
| Hydrothermal 5 h | 6.9 | 97.6 | 67.8 |
| Hydrothermal 9 h | 8.4 | 98.7 | 71.6 |
| Hydrothermal 12 h | 6.2 | 98.3 | 73.7 |
| Hydrothermal 18 h | 13.8 | 98.9 | 46.3 |
| Hydrothermal 24 h | 13.0 | 98.7 | 48.9 |

In the embodiment, the modified zeolite samples of embodiment 1 and embodiment 6 are used respectively for the liquid phase epoxidation. See Table 1 for the results. It can be seen from Table 1 that if the sodium ion modified TS-1 zeolite prepared by the method of the present invention is used in the liquid phase epoxidation, the conversion rate of hydrogen peroxide is reduced, and the utilization rate of hydrogen peroxide is also reduced. The selectivity improvement effect of the sodium ion modified TS-1 zeolite in the liquid phase epoxidation is actually the result of neutralizing a small amount of weakly acidic sites on the surface of the zeolite by the sodium ions. These are consistent with the results obtained on the sodium exchange TS-1 zeolite by J. Catal., 1995, 151, 77-86. The important information to be emphasized in the reference embodiment is: the alkali metal ion modified framework titanium active site obtained by the method of the present invention, i.e., the degree controlled hydrothermal modification method of the alkali metal hydroxide solution, is also not conducive to the liquid phase oxidation reaction. The presence of the sodium ions on the silicon hydroxyl near the framework titanium hinders the liquid phase oxidation reaction (reduces the conversion rate), but is relatively conducive to the self-decomposition reaction of hydrogen peroxide (reduces the utilization rate). It can be seen that the experimental results confirm that the framework titanium active site modified by the alkali metal ions is conducive to the gas phase epoxidation, which is an important discovery.

Reference embodiment 7. The reference embodiment 7 is used to illustrate that the hydrothermal treatment method provided by the present invention is not applicable to the nano TS-1 matrix synthesized by the classical method.

The embodiment 1 is repeated, but in the first step of hydrothermal synthesis of the TS-1 zeolite matrix, the TS-1 matrix is synthesized according to the formula of the classical method introduced by the Chinese invention patent (application number 200910131993.5). The silicon-titanium molar ratio, the framework titanium index data, and the relative crystallinity index of the matrix meet the requirements of the present invention, but the crystal size is 200-300 nanometers (aggregates). Thus, the matrix belongs to the nanosized TS-1 and is an inapplicable matrix as mentioned above in the present invention. However, in order to illustrate it with the reaction results, the nano TS-1 is modified according to the procedure introduced in the embodiment. Then, for the modified TS-1 zeolite, the performance of gas phase epoxidation of propylene and hydrogen peroxide in the fixed bed reactor is as follows: for the nano TS-1 matrix, the conversion rate of propylene is 7.3%, the PO selectivity is 76.7% and the utilization rate of hydrogen peroxide is 36.5%; and in case of the modified nano TS-1 zeolite, however, the conversion rate of propylene is 0.42%, the PO selectivity is 86.2% and the utilization rate of hydrogen peroxide is 2.1%.

The invention claimed is:

1. A fluidized reaction method for synthesizing propylene oxide by gas phase epoxidation of propylene and hydrogen peroxide, wherein a fluidized epoxidation reaction is conducted at normal pressure and temperature above 100° C.; the raw materials of propylene and hydrogen peroxide are directly mixed in gas phase; feed gas enables catalyst to be fluidized in an epoxidation reactor; the catalyst is a microspherical catalyst formed with a kind of alkali metal ion modified titanium silicalite zeolite TS-1; the alkali metal ion modified titanium silicalite zeolite TS-1 has the characteristic that alkali metal ions are reserved on the silicon hydroxyl of a modified TS-1 zeolite to modify the local environment of the framework titanium; therefore, an infrared characteristic absorption band of framework titanium active site of the alkali metal ion modified titanium silicalite zeolite TS-1 appears in a range above 960 $cm^{-1}$ and below 980 $cm^{-1}$;

the preparation steps of the catalyst are as follows:

at first step: selecting a TS-1 zeolite matrix;

the TS-1 zeolite matrix shall meet the following requirements: the crystal size is ≥0.3 micron; the silicon-titanium molar ratio is ≤200; the index value of the framework titanium content is ≥0.4; and relative crystallinity is ≥85%;

at second step: preparing an alkali metal hydroxide modification solution;

the concentration of the alkali metal hydroxide modification solution is 0.05-0.2 mol/L;

at third step: conducting a degree controlled hydrothermal treatment on the TS-1 zeolite matrix by using the alkali metal hydroxide modification solution;

the ratio of volume of the alkali metal hydroxide modification solution to weight of the TS-1 zeolite matrix is in the range of 5-15 ml/g; hydrothermal modification temperature is 100° C.-200° C.; hydrothermal modification time is 10-20 hours;

at fourth step: conducting post-treatment on the hydrothermally modified TS-1 zeolite;

the post-treatment comprises solid-liquid separation, washing, drying and calcining; in a washing process, modified TS-1 zeolite wet material obtained by solid-liquid separation is washed by using a low concentration alkali metal hydroxide solution, and the degree of washing is satisfactory when no precipitate appears after the washing solution is neutralized with acid; the concentration of the alkali metal hydroxide solution for washing is 0.001-0.05 mol/L;

at fifth step: molding the alkali metal ion modified titanium silicalite zeolite TS-1 as microspherical catalyst by a spray forming method, wherein the spray forming method is as follows:

(1) the suspension of the modified TS-1 zeolite is prepared with the acid-catalyzed hydrolysis solution of tetraethyl orthosilicate: tetraethyl orthosilicate is added to deionized water under stirring; then, concentrated nitric acid is added dropwise to the solution to hydrolyze the tetraethyl orthosilicate at room temperature under acidic conditions and distill the alcohol to obtain a binder glue solution; then, an alkali metal ion modified TS-1 zeolite is dispersed in the binder glue solution, and the dispersion liquid is treated with a colloid mill to make the D90 size value of the particles in the zeolite suspension less than or equal to 8 microns, thereby obtaining a zeolite suspension for spray forming, wherein the pH of the tetraethyl orthosilicate hydrolyzed at room temperature under the acidic conditions is 3.0-4.0; alcohol distilling conditions are: temperature is 55-60° C.; the total solid content in the zeolite suspension is 20-35 wt %; the percentage of the alkali metal ion modified TS-1 zeolite in all of the solid matters in the zeolite suspension is 40-80 wt %;

(2) a spray drying tower is used for spray forming of the suspension: the temperature of hot air entering the tower is 350° C., and the temperature of exhaust air exiting the tower is not less than 100° C.;

(3) the spray forming product collected from the spray drying tower are dried and calcined to obtain a microspherical catalyst, wherein drying is conducted at 110° C. until the dry basis content is not less than 90 wt %; calcining temperature is 540-600° C., and calcining time is 1-10 hours.

2. The fluidized reaction method for synthesizing propylene oxide by gas phase epoxidation of propylene and hydrogen peroxide according to claim 1, wherein in the first step, the crystal size of the TS-1 zeolite matrix is ≥0.5 micron; the silicon-titanium molar ratio is ≤100; the index value of the framework titanium content is ≥0.45; and the relative crystallinity is ≥90%.

3. The fluidized reaction method for synthesizing propylene oxide by gas phase epoxidation of propylene and hydrogen peroxide according to claim 1, wherein in the second step, the concentration of the alkali metal hydroxide modification solution is 0.08-0.15 mol/L; and the alkali metal hydroxide is lithium hydroxide, sodium hydroxide or potassium hydroxide.

4. The fluidized reaction method for synthesizing propylene oxide by gas phase epoxidation of propylene and hydrogen peroxide according to claim 1, wherein in the third step, the ratio of volume of the alkali metal hydroxide modification solution to weight of the TS-1 zeolite matrix is in the range of 8-12 ml/g zeolite; hydrothermal modification temperature is 150° C.-190° C.; and hydrothermal modification time is 15-20 hours.

5. The fluidized reaction method for synthesizing propylene oxide by gas phase epoxidation of propylene and hydrogen peroxide according to claim 3, wherein in the third step, the ratio of volume of the alkali metal hydroxide modification solution to weight of the TS- 1 zeolite matrix is in the range of 8-12 ml/g zeolite; hydrothermal modification temperature is 150° C-190° C.; and hydrothermal modification time is 15-20 hours.

6. The fluidized reaction method for synthesizing propylene oxide by gas phase epoxidation of propylene and hydrogen peroxide according to claim 1, wherein in the fourth step, the concentration of the alkali metal hydroxide solution used for washing is 0.005-0.04 mol/L; the alkali metal hydroxide is lithium hydroxide, sodium hydroxide or potassium hydroxide; the drying temperature is 80-120° C., and the drying time is decided based on the dry basis content of the sample not less than 90%; the final calcining temperature is 400-550° C., and the constant temperature time at the final calcining temperature is more than 3 hours.

7. The fluidized reaction method for synthesizing propylene oxide by gas phase epoxidation of propylene and hydrogen peroxide according to claim 4, wherein in the fourth step, the concentration of the alkali metal hydroxide solution used for washing is 0.005-0.04 mol/L; the alkali metal hydroxide is lithium hydroxide, sodium hydroxide or potassium hydroxide; the drying temperature is 80-120° C., and the drying time is decided based on the dry basis content of the sample not less than 90%; the final calcining temperature is 400-550° C., and the constant temperature time at the final calcining temperature is more than 3 hours.

8. The fluidized reaction method for synthesizing propylene oxide by gas phase epoxidation of propylene and hydrogen peroxide according to claim 6, wherein in the fourth step, the concentration of the alkali metal hydroxide solution used for washing is 0.005-0.03 mol/L.

9. The fluidized reaction method for synthesizing propylene oxide by gas phase epoxidation of propylene and hydrogen peroxide according to claim 7, wherein in the fourth step, the concentration of the alkali metal hydroxide solution used for washing is 0.005-0.03 mol/L.

10. The fluidized reaction method for synthesizing propylene oxide by gas phase epoxidation of propylene and hydrogen peroxide according to claim 1, wherein in the fifth step, the percentage of the alkali metal ion modified TS-1 zeolite in all of the solid matters in the zeolite suspension is 50-70 wt. %.

* * * * *